US011939403B2

(12) United States Patent
Lokey et al.

(10) Patent No.: US 11,939,403 B2
(45) Date of Patent: Mar. 26, 2024

(54) PEPTIDE-PEPTOID SCAFFOLDS

(71) Applicant: The Regents of the University of California, Oakland, CA (US)

(72) Inventors: R. Lokey, Santa Cruz, CA (US); Akihiro Furukawa, Tokyo (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/366,822

(22) Filed: Jul. 2, 2021

(65) Prior Publication Data

US 2022/0002346 A1 Jan. 6, 2022

Related U.S. Application Data

(60) Provisional application No. 63/047,788, filed on Jul. 2, 2020.

(51) Int. Cl.
*C07K 7/54* (2006.01)
*C07K 7/64* (2006.01)

(52) U.S. Cl.
CPC ..................... *C07K 7/54* (2013.01)

(58) Field of Classification Search
CPC ................. C07K 7/54; C07K 7/64
See application file for complete search history.

(56) References Cited

PUBLICATIONS

Fouche et al., "Design and Development of a Cyclic Decapeptide Scaffold with Suitable Properties for Bioavailability and Oral Exposure," Chem MedChem, 2016, 11: 1048-1059. (Year: 2016).*
Fouche et al., Pharmacokinetic Studies around the Mono- and Difunctionalization of a Bioavailability Cyclic Decapeptide Scaffold, ChemMedChem, 2016, 11: 1060-1068. (Year: 2016).*
Furukawa et al., "Drug-Like Properties in Macrocycles above MW 1000: Backbone Rigidity versus Side-Chain Lipophilicity," Angewandte Chemie International Edition, online Nov. 16, 2020, 59: 21571-21577. (Year: 2020).*
Nakajima, N. et al., "Multicanonical Ensemble Generated by Molecular Dynamics Simulation for Enhanced Conformational Sampling of Peptides", J. Phys. Chem. B., (1997) vol. 101, pp. 817-824. PubMed PMID: WOS: A1997WL11000018.
Ono, S. et al., "Conformation and Permeability: Cyclic Hexapeptide Diastereomers", J. Chem. Inf. Model., (2019) vol. 59, pp. 2952-2963. Epublication May 1, 2019. doi: 10.1021/acs.jcim.9b00217. PubMed PMID: 31042375.
Overington, J.P. et al., "How many drug targets are there?", Nat. Rev. Drug Discov., (2006) vol. 5, pp. 993-996. doi: 10.1038/nrd2199. PubMed PMID: 17139284.
Malovannaya, A. et al., "Analysis of the human endogenous coregulator complexome", Cell, (2011) vol. 145, pp. 787-799. doi: 10.1016/j.cell.2011.05.006. PubMed PMID: 21620140; PMCID: 3131083.
Colby, D.W. et al., "Potent inhibition of huntingtin aggregation and cytotoxicity by a disulfide bond-free single-domain intracellular antibody", Proc Natl. Acad. Sci. U S A, (2004) vol. 101, No. 51, p. 17616-17621 and Corrections, Proc. Natl. Acad. Sci. U S A, (2005) vol. 102, No. 3, p. 955. doi: 10.1073/pnas.0408134101. PubMed PMID: 15598740; PMCID: 539732.
Kenne E. & Renne T., "Factor XII: a drug target for safe interference with thrombosis and inflammation", Drug Discovery Today, (2014) vol. 19, No. 9, pp. 1459-1464. doi: 10.1016/j.drudis.2014.06.024. PubMed PMID: 24993156.
Reichert, J.M. & Dhimolea, E., "Foundation review: The future of antibodies as cancer drugs", Drug Discovery Today, (2012) vol. 17, No. 17/18, pp. 954-963. doi: 10.1016/j.drudis.2012.04.006. PubMed PMID: 22561895.
Passioura T. et al., "Selection-based Discovery of Druglike Macrocyclic Peptides", Annu. Rev. Biochem., (2014) vol. 83, pp. 727-752 & Contents pp. v-vii. doi: 10.1146/annurev-biochem-060713-035456. PubMed PMID: 24580641.
Kawamoto, S.A., "Design of Triazole-Stapled BCL9 alpha-Helical Peptides to Target the beta-Catenin/B-Cell CLL/lymphoma 9 (BCL9) Protein-Protein Interaction", J. Med. Chem., (2012) vol. 55, pp. 1137-1146. doi: 10.1021/jm201125d. PubMed PMID: 22196480; PMCID: 3286869.
Madden, M.M. et al., "Synthesis of cell-permeable stapled peptide dual inhibitors of the p53-Mdm2/Mdmx interactions via photoinduced cycloaddition", Bioorg. Med. Chem. Lett., (2011) vol. 21, pp. 1472-1475. doi: 10.1016/j.bmcl.2011.01.004. PubMed PMID: 21277201; PMCID: 3057119.
Moellering, R.E. et al., "Direct inhibition of the NOTCH transcription factor complex", Nature, (2009) vol. 462, pp. 182-188 & Methods (2 pages) and Erratum, Nature, (2010) vol. 463, p. 384. doi: 10.1038/nature08543. PubMed PMID: 19907488; PMCID: 2951323.
Liu, T., et al., "Synthesis and screening of a cyclic peptide library: Discovery of small-molecule ligands against human prolactin receptor", Bioorg. Med. Chem., (2009) vol. 17, pp. 1026-1033. doi: 10.1016/j.bmc.2008.01.015. PubMed PMID: 18234500; PMCID: 2662701.
Gavenonis, J. et al., "Comprehensive analysis of loops at protein-protein interfaces for macrocycle design", Nat. Chem. Biol., (2014) vol. 10, pp. 716-722 & Online Methods (1 page). doi: 10.1038/nchembio.1580. PubMed PMID: 25038791; PMCID: PMC4138238.
Qian, Z. et al., "Targeting intracellular protein-protein interactions with cell-permeable cyclic peptides", Curr. Opin. Chem. Biol., (2017) vol. 38, pp. 80-86. doi: 10.1016/j.cbpa.2017.03.011. PubMed PMID: 28388463; PMCID: PMC5474178.
Kling, A. et al., "Antibiotics: Targeting DnaN for tuberculosis therapy using novel griselimycins", Science, (2015) vol. 348, No. 6239, pp. 1106-1112 & 1 supplemental p. doi: 10.1126/science. aaa4690. PubMed PMID: 26045430.
Schwochert, J. et al., "Stereochemistry Balances Cell Permeability and Solubility in the Naturally Derived Phepropeptin Cyclic Peptides", ACS Med. Chem. Lett., (2016) vol. 7, pp. 757-761. doi: 10.1021/acsmedchemlett.6b00100. PubMed PMID: 27563399; PMCID: PMC4983725.

(Continued)

Primary Examiner — Julie Ha
(74) Attorney, Agent, or Firm — Nixon & Vanderhye, PC; Lars H. Genieser

(57) ABSTRACT

Molecular scaffolds, including cyclic peptides, that have high (large) cell permeability.

27 Claims, 11 Drawing Sheets

(56) References Cited

PUBLICATIONS

Schwochert, J. et al., "Peptide to Peptoid Substitutions Increase Cell Permeability in Cyclic Hexapeptides", Org. Lett., (2015) vol. 17, pp. 2928-2931. doi: 10.1021/acs.orglett.5b01162. PubMed PMID: 26046483.

Hewitt, W.M. et al., "Cell-Permeable Cyclic Peptides from Synthetic Libraries Inspired by Natural Products", J. Am. Chem. Soc., (2015), vol. 137, No. 2, pp. 715-721. doi: 10.1021/ja508766b. PubMed PMID: 25517352.

Bockus, A.T. et al., "Probing the Physicochemical Boundaries of Cell Permeability and Oral Bioavailability in Lipophilic Macrocycles Inspired by Natural Products", J. Med. Chem., (2015) vol. 58, pp. 4581-4589. doi: 10.1021/acs.jmedchem.5b00128. PubMed PMID: 25950816.

Bockus, A.T. et al., "Going Out on a Limb: Delineating The Effects of beta-Branching, N-Methylation, and Side Chain Size on the Passive Permeability, Solubility, and Flexibility of Sanguinamide A Analogues", J. Med. Chem., (2015), vol. 58, pp. 7409-7418. doi: 10.1021/acs.jmedchem.5b00919. PubMed PMID: 26308180.

Ahlbach, C.L. et al., "Beyond cyclosporine A: conformation-dependent passive membrane permeabilities of cyclic peptide natural products", Future Med. Chem., (2015) vol. 7, No. 16, pp. 2121-2130. doi: 10.4155/fmc. 15.78. PubMed PMID: 26067057; PMCID: PMC5186412.

Schwochert, J. et al., "Revisiting N-to-O Acyl Shift for Synthesis of Natural Product-like Cyclic Depsipeptides", Org. Lett., (2014) vol. 16, No. 23, pp. 6088-6091. doi: 10.1021/01503170b. PubMed PMID: 25412436. 11.

Rand, A.C. et al., "Optimizing PK properties of cyclic peptides: the effect of side chain substitutions on permeability and clearance", Med. Chem. Commun., (2012) vol. 3, pp. 1282-1289. doi: 10.1039/c2md20203d. PubMed PMID: WOS:000310423600012.

Rezai, T. et al., "Conformational Flexibility, Internal Hydrogen Bonding, and Passive Membrane Permeability: Successful in Silico Prediction of the Relative Permeabilities of Cyclic Peptides", J. Am. Chem. Soc., (2006) vol. 128, pp. 14073-14080. doi: 10.1021/ja063076p. PubMed PMID: WOS:000241519600043.

Rezai, T. et al., "Testing the Conformational Hypothesis of Passive Membrane Permeability Using Synthetic Cyclic Peptide Diastereomers", J. Am. Chem. Soc., (2006) vol. 128, pp. 2510-2511. doi: 10.1021/ja0563455. PubMed PMID: WOS:000235787200004.

Wang, C.K. et al., "Rational design and synthesis of an orally bioavailable peptide guided by NMR amide temperature coefficients", Proc. Natl. Acad. Sci. U S A., (2014) vol. 111, No. 49, pp. 17504-17509. doi: 10.1073/pnas. 1417611111. PubMed PMID: 25416591; PMCID: 4267368.

Nielsen, D.S. et al., "Improving On Nature: Making a Cyclic Heptapeptide Orally Bioavailable", Angew. Chem. Int. Ed. Engl., (2014) vol. 53, pp. 12059-12063. doi: 10.1002/anie.201405364. PubMed PMID: 25219505.

Wang, C.K. et al., "Exploring experimental and computational markers of cyclic peptides: Charting islands of permeability", Eur. J. Med. Chem., (2015) vol. 97, pp. 202-213. doi: 10.1016/j.ejmech. 2015.04.049. PubMed PMID: BCI:BCI201500534985.

Driggers, E.M. et al., "The exploration of macrocycles for drug discovery—an underexploited structural class", Nat. Rev. Drug Disc., (2008) vol. 7, pp. 608-624. doi: 10.1038/nrd2590. PubMed PMID: WOS:000257268200015.

Gao, Y. & Kodadek, T., "Direct Comparison of Linear and Macrocyclic Compound Libraries as a Source of Protein Ligands", ACS Combinatorial Sci., (2015) vol. 17, pp. 190-195. doi: 10.1021/co500161c. PubMed PMID: 25623285; PMCID: PMC4356041.

Sia, S.K. et al., "Short constrained peptides that inhibit HIV-1 entry", Proc. Natl. Acad. Sci. U S A, (2002) vol. 99, No. 23, p. 14664-14669. doi: 10.1073/pnas.232566599. PubMed PMID: 12417739; PMCID: PMC137476.

Di, L., "Strategic Approaches to Optimizing Peptide ADME Properties", Aaps J., (2015) vol. 17, No. 1, pp. 134-143. doi: 10.1208/s12248-014-9687-3. PubMed PMID: 25366889; PMCID: PMC4287298.

Nielsen, D.S. et al., "Orally Absorbed Cyclic Peptides", Chem. Rev., (2017) vol. 117, pp. 8094-8128. Epublication May 2, 20175. doi: 10.1021/acs.chemrev.6b00838. PubMed PMID: 28541045.

Dougherty, P.G. et al., "Understanding Cell Penetration of Cyclic Peptides", Chem. Rev., (2019) vol. 119, p. 10241-10287. Epublication May 1, 20194. doi: 10.1021/acs.chemrev.9b00008. PubMed PMID: 31083977; PMCID: PMC6739158.

Caron, G. et al., "Intramolecular hydrogen bonding: An opportunity for improved design in medicinal chemistry", Med. Res. Rev., (2019) vol. 39, pp. 1707-1729. Epublication Jan. 20, 2019. doi: 10.1002/med.21562. PubMed PMID: 30659634.

Bockus, A.T. et al., "Form and Function In Cyclic Peptide Natural Products: A Pharmacokinetic Perspective", Current Topics Med. Chem., (2013) vol. 13, pp. 821-836. PubMed PMID: 23578026.

Bockus, A.T. & Lokey, R.S., "Bioactive and Membrane-Permeable Cyclic Peptide Natural Products", in Marsault, E. & Peterson, M.L., editors, "Practical Medicinal Chemistry with Macrocycles: Design, Synthesis, and Case Studies", Hoboken, N.J., Wiley, (2017) pp. 101-132 & title page & bibliographic page.

Pye, C.R. et al., "Nonclassical Size Dependence of Permeation Defines Bounds for Passive Adsorption of Large Drug Molecules", J. Med. Chem., (2017) vol. 60, pp. 1665-1672. doi: 10.1021/acs.jmedchem.6b01483. PubMed PMID: 28059508; PMCID: PMC5677520.

Furukawa, A. et al., "Passive Membrane Permeability in Cyclic Peptomer Scaffolds Is Robust to Extensive Variation in Side Chain Functionality and Backbone Geometry", J. Med. Chem., (2016) vol. 59, No. 20, pp. 9503-9512. doi: 10.1021/acs.jmedchem.6b01246. PubMed PMID: 27690434.

White, T.R. et al., "On-resin N-methylation of cyclic peptides for discovery of orally bioavailable scaffolds", Nat. Chem. Biol. (2011) vol. 7, pp. 810-817. doi: 10.1038/nchembio.664. PubMed PMID: 21946276; PMCID: PMC3210067.

Boehm, M. et al., "Discovery of Potent and Orally Bioavailable Macrocyclic Peptide-Peptoid Hybrid CXCR7 Modulators", J. Med. Chem., (2017) vol. 60, pp. 9653-9663. doi: 10.1021/acs.jmedchem. 7b01028. PubMed PMID: 29045152.

Zuckermann, R.N. et al., "Efficient Method for the Preparation of Peptoids [Oligo(N-substituted glycines)] by Submonomer Solid-Phase Synthesis", J. Am. Chem. Soc., (1992) vol. 114, pp. 10646-10647. doi: DOI 10.1021/ja00052a076. PubMed PMID: WOS:A1992KD71700076.

Naylor, M.R. et al., "Lipophilic Permeability Efficiency (LPE) Reconciles the Opposing Roles of Lipophilicity in Membrane Permeability and Aqueous Solubility", J. Med. Chem., (2018) vol. 61, p. 11169-11182. Epublication Nov. 5, 2018. doi: 10.1021/acs. jmedchem.8b01259. PubMed PMID: 30395703.

Witek, J. et al., "Rationalization of the Membrane Permeability Differences in a Series of Analogue Cyclic Decapeptides", J. Chem. Inf. Model., (2019) vol. 59, pp. 294-308. Epublication Nov. 20, 2018. doi: 10.1021/acs. jcim.8b00485. PubMed PMID: 30457855.

El Tayar, N. et al., "Solvent-Dependent Conformation and Hydrogen-Bonding Capacity of Cyclosporin A: Evidence from Partition Coefficients and Molecular Dynamics Simulations", J. Med. Chem., (1993) vol. 36, pp. 3757-3764. PubMed PMID: 8254605.

Witek, J. et al., "Interconversion Rates between Conformational States as Rationale for the Membrane Permeability of Cyclosporines", ChemPhysChem, (2017) vol. 18, pp. 3309-3314. doi: 10.1002/cphc. 201700995. PubMed PMID: 28921848.

Witek, J. et al., "Kinetic Models of Cyclosporin A in Polar and Apolar Environments Reveal Multiple Congruent Conformational States", J. Chem. Inf. Model., (2016) vol. 56, pp. 1547-1562. doi: 10.1021/acs.jcim.6600251. PubMed PMID: 27387150.

Kessler, H. et al., "Complexation and medium effects on the conformation of cyclosporin A studied by NMR spectroscopy and molecular dynamics calculations", Biochem. Pharmacol., (1990) vol. 40, No. 1, pp. 169-173. PubMed PMID: 2164815.

(56) References Cited

PUBLICATIONS

Wang, C.K. et al., "Conformational Flexibility Is a Determinant of Permeability for Cyclosporin", J. Phys. Chem. B., (2018) vol. 122, pp. 2261-2276. doi: 10.1021/acs.jpcb.7b12419. PubMed PMID: 29400464.

* cited by examiner

PEPTIDE-PEPTOID SCAFFOLDS

This application claims the benefit of U.S. Provisional Application No. 63/047,788, filed Jul. 2, 2020, which is hereby incorporated by reference in its entirety.

This invention was made with Government support under Grant No. GM131135 awarded by the National Institutes of Health. The Government has certain rights in the invention.

FIELD

An embodiment of the invention pertains to molecular scaffolds, including cyclic peptides, that have high (large) cell permeability.

BACKGROUND

The discovery and validation of new therapeutic targets can outpace the finding of inhibitors against them. (Overington J P et al. *How many drug targets are there?* Nat Rev Drug Discov. (2006) 5, 993-6. doi: 10.1038/nrd2199. PubMed PMID: 17139284; Malovannaya A et al. *Analysis of the human endogenous coregulator complexome.* Cell. (2011) 145, 787-99. doi: 10.1016/j.cell.2011.05.006. PubMed PMID: 21620140; PMCID: 3131083.) These targets can include protein-protein interactions (PPIs), which lack the binding pockets found in enzymes and receptors and, thus, can be "undruggable" by conventional small molecules. Although PPIs can be inhibited by large molecules and protein complexes, such as antibodies, the inability to cross cell membranes fundamentally limits the scope of antibodies and other biologics to extracellular targets, leaving the much larger set of intracellular PPIs out of reach. (Colby D W et al. *Potent inhibition of huntingtin aggregation and cytotoxicity by a disulfide bond-free single-domain intracellular antibody.* Proc Natl Acad Sci USA. (2004) 101, 17616-21. doi: 10.1073/pnas.0408134101. PubMed PMID: 15598740; PMCID: 539732; Kenne E & Renne T. *Factor XII: a drug target for safe interference with thrombosis and inflammation.* Drug Discov Today. (2014). doi: 10.1016/j.drudis.2014.06.024. PubMed PMID: 24993156; Reichert J M & Dhimolea E. *The future of antibodies as cancer drugs.* Drug Discov Today. (2012) 17, 954-63. doi: 10.1016/j.drudis.2012.04.006. PubMed PMID: 22561895.) For drug molecules, cell permeability and oral bioavailability become increasingly difficult to achieve as molecular weight increases beyond about 600 Da (Dalton, g/mol).

SUMMARY

An embodiment of the invention includes a compound of the structure

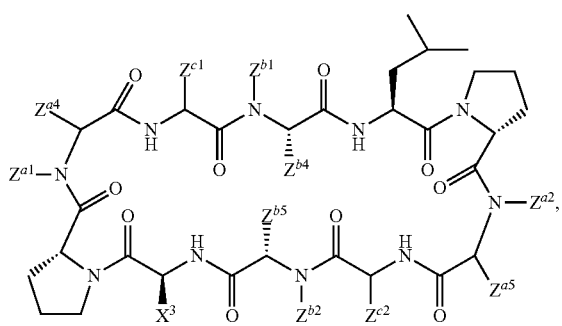

of which $Z^{a1}$ is $X^1$ or methyl ($CH_3$—), $Z^{a2}$ is $X^2$ or methyl ($CH_3$—), $Z^{a4}$ is hydrogen (H—) or 2-methylpropyl

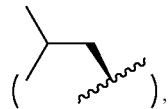, $Z^{a5}$ is hydrogen (H—) or 2-methylpropyl

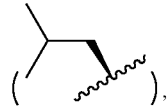, $Z^{b1}$ is $X^1$ or methyl ($CH_3$—), $Z^{b2}$ is $X^2$ or methyl ($CH_3$—), $Z^{b4}$ is hydrogen (H—) or methyl ($CH_3$—), $Z^{b5}$ is hydrogen (H—) or methyl ($CH_3$—), $Z^{c1}$ is 2-methylpropy

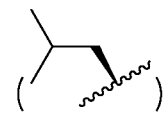

or methyl ($CH_3$—), $Z^{c2}$ is 2-methylpropyl

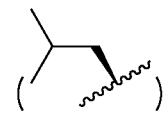

or methyl ($CH_3$—), $X^1$ is ethyl (Et-)

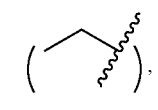, 2-propoxy-3-propyl

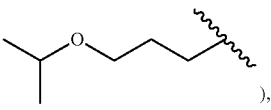, or (1,3-benzodioxol-5-yl)-methyl
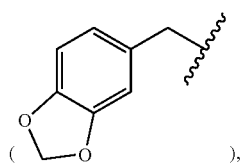
X² is pentyl
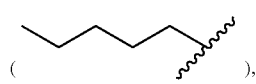
cyclohexylmethyl
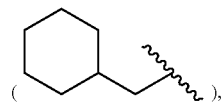 [SMILES: *CC1CCCCC1]
or (oxan-4-yl)methyl
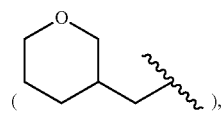 [SMILES: *CC1CCCOC1]
and
X³ is methyl
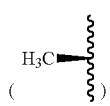
or benzyl
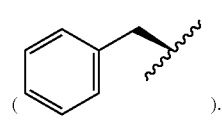
In an embodiment of the invention, the compound is of the structure
Library A
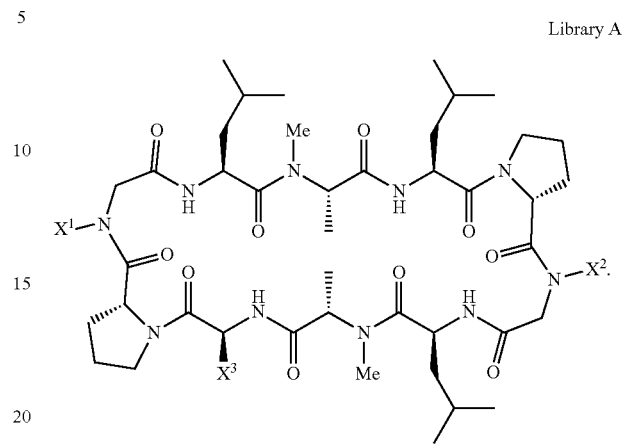
For example, the compound is of the structure
A03
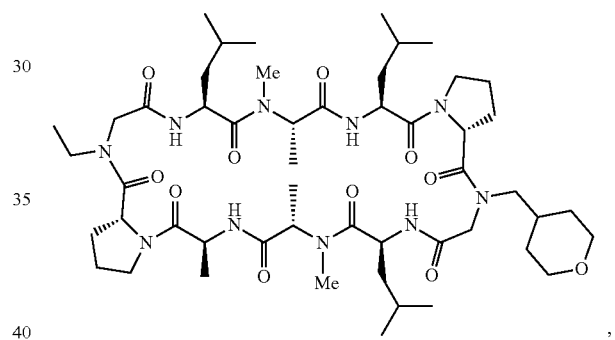
A09
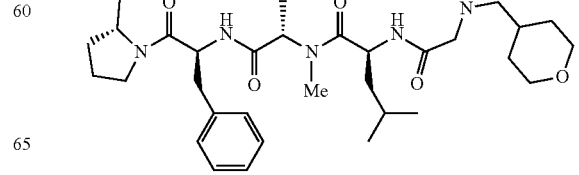
, or

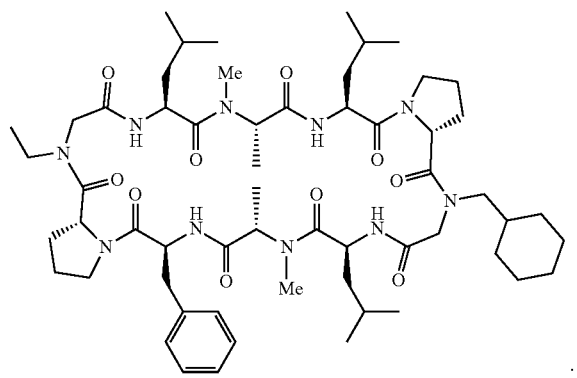

In an embodiment of the invention, the compound is of the structure

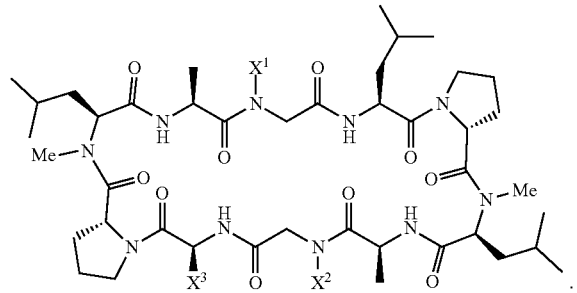

Library B

For example, the compound is of the structure

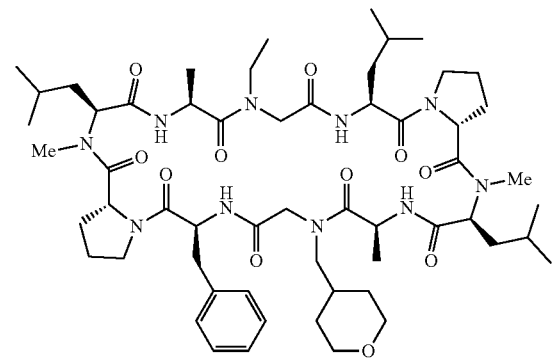

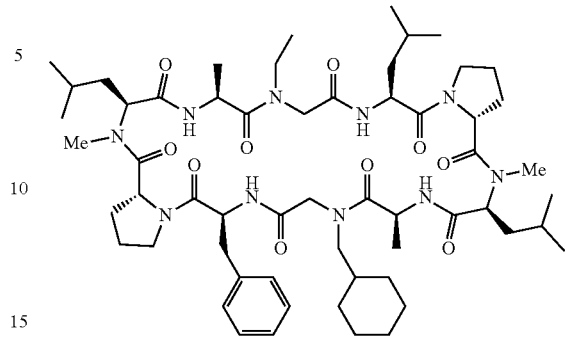

, or

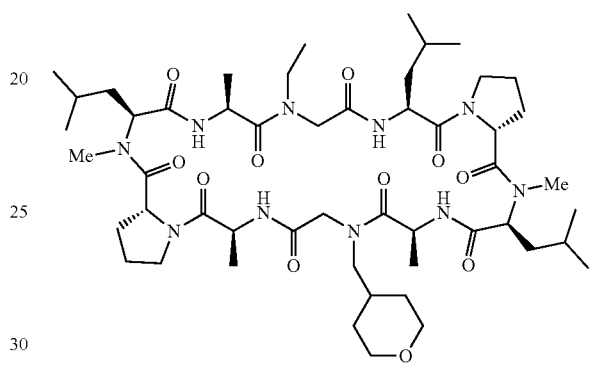

A method of the invention includes designing and preparing a permeable cyclic decapeptide-peptoid ligand. The permeable cyclic decapeptide-peptoid ligand is of a class of ligands of the structure

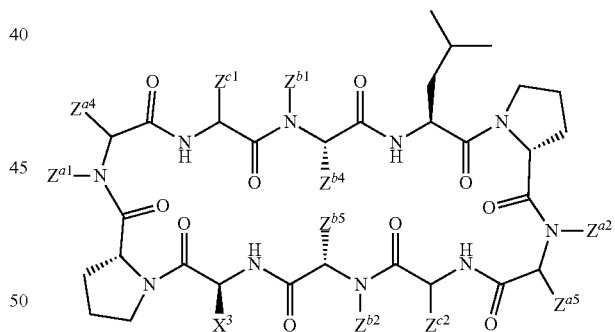

of which the variable substituents can be as above. The method includes determining whether a dissociation constant of the ligands of the class and a therapeutic target at physiological conditions is minimized by the ligands being rigid or flexible. If the dissociation constant is minimized by the ligands of the class being rigid, then the following are selected to obtain a rigid permeable cyclic decapeptide-peptoid ligand: $Z^{a4}$ is H; $Z^{b1}$ is $CH_3$; $Z^{a5}$ is H; and $Z^{b2}$ is $CH_3$. If the dissociation constant is minimized by the ligands of the class being flexible, then the following are selected to obtain a flexible permeable cyclic decapeptide-peptoid ligand: $Z^{a4}$ is 2-methylpropyl; $Z^{b1}$ is $X^1$; $Z^{a5}$ is 2-methylpropyl; and $Z^{b2}$ is $X^2$. The permeable cyclic decapeptide-peptoid ligand can then be synthesized.

In a method, if the dissociation constant is minimized by the ligands of the class being rigid, then the structure of the permeable cyclic decapeptide-peptoid ligand is selected as Library A

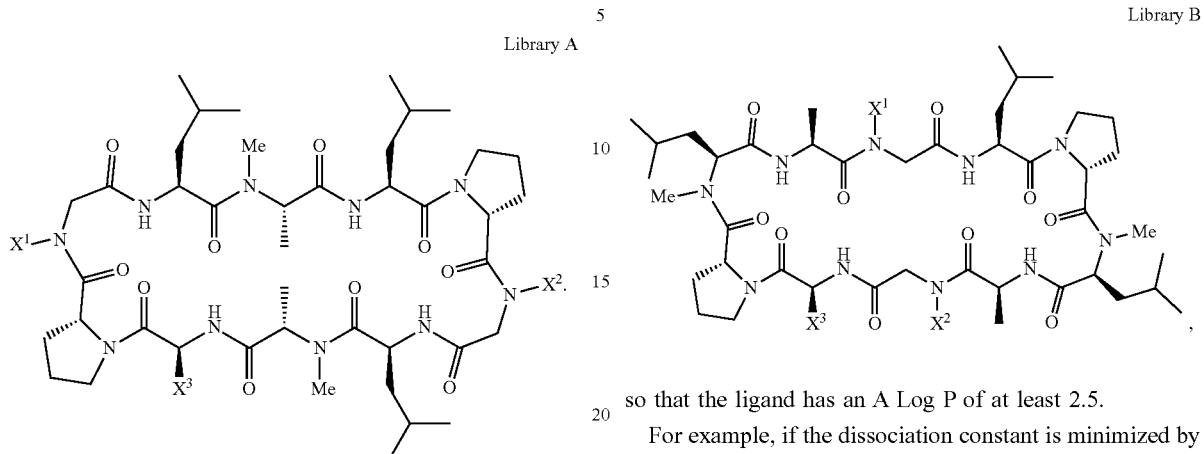

If the dissociation constant is minimized by the ligands of the class being flexible, then the structure of the permeable cyclic decapeptide-peptoid ligand is selected as Library B In a method, if the dissociation constant is minimized by the ligands of the class being rigid, then the structure of the permeable cyclic decapeptide-peptoid ligand is selected as Library A so that the ligand has an A Log P of at most 2.5. If the dissociation constant is minimized by the ligand being flexible, then the structure of the permeable cyclic decapeptide-peptoid ligand is selected as Library B so that the ligand has an A Log P of at least 2.5.

For example, if the dissociation constant is minimized by the ligand being rigid, then the permeable cyclic decapeptide-peptoid ligand can be selected as

A03 or

A09

For example, if the dissociation constant is minimized by the ligand being flexible, then the permeable cyclic decapeptide-peptoid ligand can be selected as

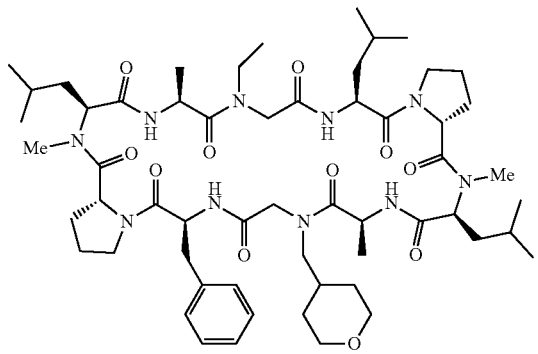

B09

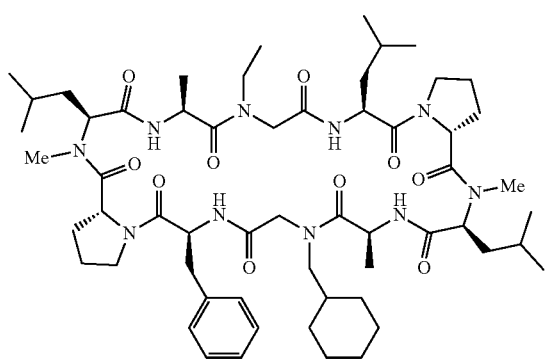

or

B08

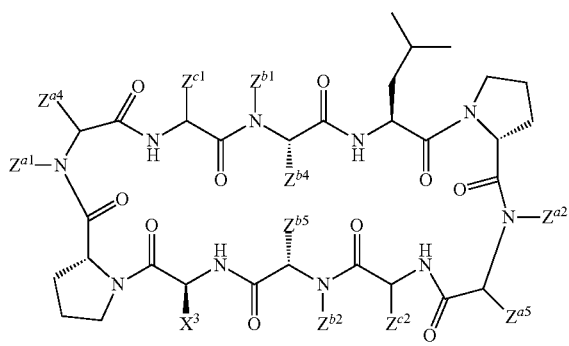

A method of the invention includes designing and preparing a permeable cyclic decapeptide-peptoid ligand. The permeable cyclic decapeptide-peptoid ligand is of the structure of which the variable substituents can be as above. The method includes determining whether a required minimum aqueous solubility of the ligand requires the ligand to be of an A Log P of at most 1.9 or whether the required minimum aqueous solubility of the ligand allows the ligand to be of an A Log P of greater than 1.9. If the ligand is required to be of an A Log P of at most 1.9, then the following are selected: $Z^{a4}$ is H; $Z^{b1}$ is $CH_3$; $Z^{a5}$ is H; and $Z^{b2}$ is $CH_3$. If the ligand is allowed to be of an A Log P of greater than 1.9, then the following are selected: $Z^{a4}$ is 2-methylpropyl; $Z^{b1}$ is $X^1$; $Z^{a5}$ is 2-methylpropyl; and $Z^{b2}$ is $X^2$. The permeable cyclic decapeptide-peptoid ligand can then be synthesized.

In a method, if the ligand is required to be of an A Log P of at most 1.9, then the structure of the ligand is selected as Library A

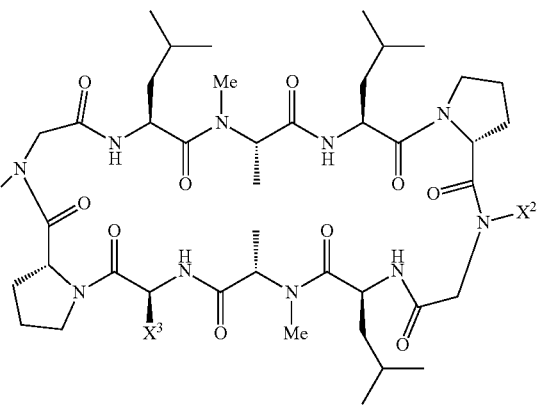

to be of an A Log P of at most 1.9. If the ligand is allowed to be of an A Log P of greater than 1.9, then the structure of the ligand is selected as Library B

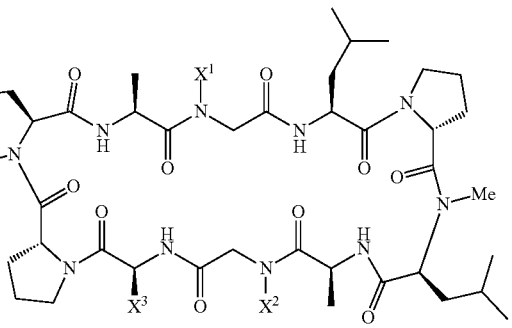

to be of an A Log P of greater than 1.9.

For example, if the ligand is required to be of an A Log P of at most 1.9, then the structure of the ligand can be selected as

A03

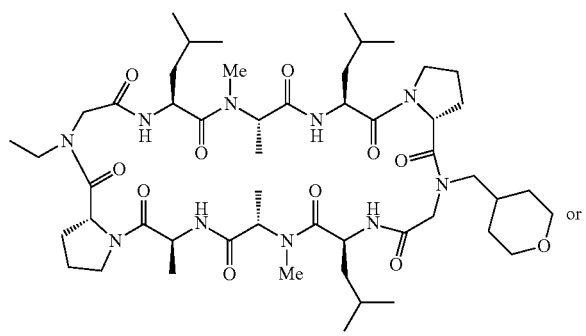

or

-continued

A09

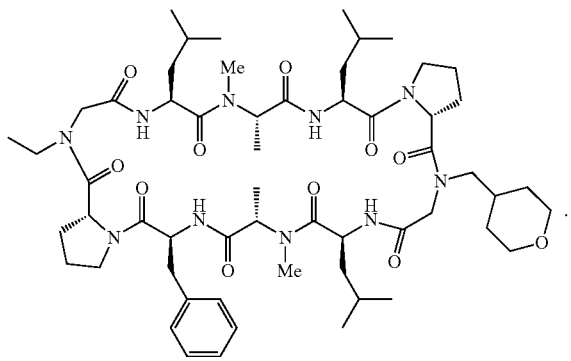

For example, if the ligand is allowed to be of an A Log P of greater than 1.9, then the structure of the ligand can be selected as

B08

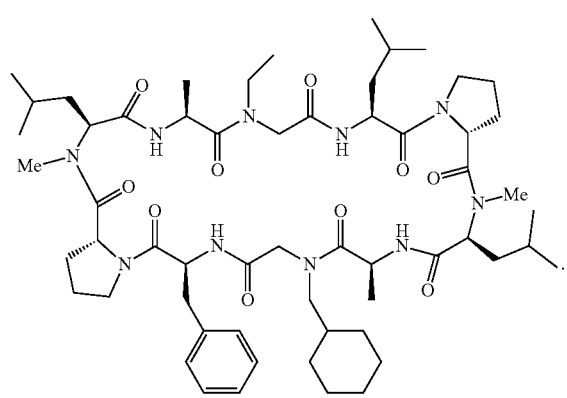

DETAILED DESCRIPTION

Figure 1A:
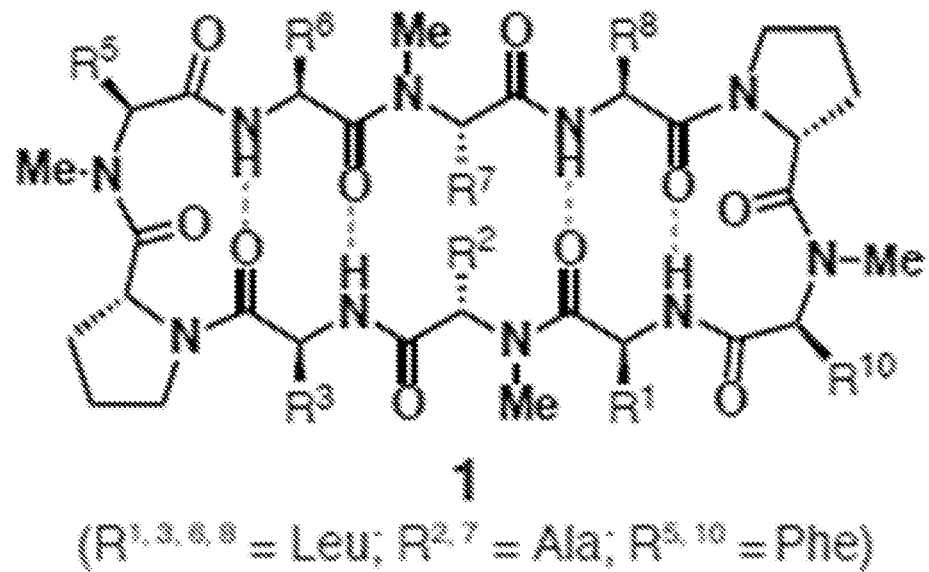
FIG. 1A. The structure of a cyclic decapeptide 1 is shown.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All documents and references cited herein are incorporated by reference in their entirety as if each had been individually incorporated.

The embodiments set forth in this specification are exemplary and do not limit the invention. Other embodiments can be utilized and changes can be made. As used in this specification, the singular forms "a", "an", and "the" include the plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features.

Large molecules (e.g., having a molecular weight greater than 1000 Da) are often cell-impermeable. Certain cyclic peptides defy the trend of lesser cell permeability and oral bioavailability with increasing molecular weight over about 600 Da; these cyclic peptides can show high (large) passive permeability and oral bioavailability (BA) even with molecular weights exceeding 1000 Da. However, such cyclic peptides can be highly complex macrocycles or cyclic peptides that are not easily diversified. Presented herein are methods for adding peptoid units to cyclic decapeptides that allow for diversification by inserting a variety of different substituents at the peptoid position. For example, based on a parent cyclic decapeptide, two Libraries (Library A and Library B) of distinct scaffolds having pairs of N-methyl amino acids substituted with N-alkylglycine (peptoid) residues were generated. The effects of these substitutions on physico-chemical, absorption, distribution, metabolism, and excretion (ADME), and pharmokinetic (PK) properties were investigated. NMR studies, corroborated by molecular dynamics (MD) simulations, showed that peptoid substitutions within the beta-turns of the macrocycle preserved the rigidity of the parent scaffold, whereas peptoid substitutions in the opposing beta-strands led to "chameleonic" species that were rigid in chloroform (a less polar or nonpolar, low (small) dielectric solvent), but highly flexible in water (a more polar or polar, high (large) dielectric solvent). An example of a low dielectric environment is the cell membrane. Both rigid and chameleonic peptoid substitutions led to species with high passive membrane permeabilities over a wide lipophilicity range, although they had low oral BA, because of high efflux and fast metabolic clearance. Oral dosing in the presence of both cytochrome P450 and P-glycoprotein (P-gp) inhibitors had a strong synergistic effect, causing a dramatic increase in oral BA. Scaffold rigidity afforded high membrane permeability at the low (small) end of the lipophilicity continuum, whereas flexible scaffolds required higher (larger) lipophilicities to achieve the same permeability. These findings indicated that modulating lipophilicity can be used to engineer positive (favorable) ADME properties into both rigid and flexible macrocyclic peptides, and that scaffold rigidity can be used to "tune" the optimal lipophilicity window for achieving passive membrane permeability.

Set forth herein are two classes of cyclic decapeptide-peptoid scaffolds (Library A and Library B) and their compounds; compounds in each of these classes are highly membrane permeable. The Library A scaffold is rigid and the Library B scaffold can be flexible. The Library A scaffold is rigid in low-dielectric (small-dielectric) media and is rigid in high-dielectric (large-dielectric) media (such as aqueous solution). The Library B scaffold is rigid in low-dielectric (small-dielectric) media but is flexible in high-dielectric (large-dielectric) media (such as aqueous solution). Thus, the Library A and the Library B scaffolds exhibit different solvent-dependent conformational properties. Compounds (molecules) have been generated from each of the Library A and Library B scaffolds that are highly permeable across a wide range of lipophilicities, and a method enables the generation of highly permeable molecules across a wide range of lipophilicities. These compounds provide the basis for large libraries of cell permeable macrocycles that lie outside boundaries that may be associated with "druglikeness" (such as drug-likeness as predicted by Lipinski's "Rule of 5"). These compounds can include inhibitors of targets such as those associated with protein-protein interactions (PPIs). Thus, set forth herein are membrane permeable decapeptide-peptoid scaffolds and cell permeable decapeptides.

For example, such a cyclic peptide-peptide compound (e.g., a cyclic decapeptide-peptoid compound) can have a molecular weight that is at least 300, 400, 500, 600, 700, 800, 900, 1000, 1100, 1200, 1300, 1400, 1500, 1700, 2000, or 2500 Da (Dalton, g/mol) and/or that is at most 400, 500, 600, 700, 800, 900, 1000, 1100, 1200, 1300, 1400, 1500, 1700, 2000, 2500, or 3000 Da. For example, a low-dielectric (small-dielectric) (less polar) medium can have a dielectric constant that is at least 1.8 (pentane), 2, 2.4 (toluene), 3, 4, 4.3 (diethyl ether), or 4.8 (chloroform ($CHCl_3$)) and/or that is at most 2, 2.4 (toluene), 3, 4, 4.3 (diethyl ether), 4.8 (chloroform ($CHCl_3$)), or 5. For example, a high-dielectric (large-dielectric) (more polar) medium can have a dielectric constant that is at least 18 (n-butanol and isopropyl alcohol), 20 (n-propanol), 25 (ethanol), 30, 33 (methanol), 38 (acetonitrile (ACN)), 40, 47 (dimethylsulfoxide (DMSO)), 50, 60, 70, 80 (water ($H_2O$)), or 90 and/or that is at most 20 (n-propanol), 25 (ethanol), 30, 33 (methanol), 38 (acetonitrile (ACN)), 40, 47 (dimethylsulfoxide (DMSO)), 50, 60, 70, 80 (water ($H_2O$)), 90, or 100.

Cyclic peptides can achieve the biochemical potency and specificity of biologics, even against challenging targets such as PPIs. (Passioura T et al. *Selection-based discovery of druglike macrocyclic peptides*. Annu Rev Biochem. (2014) 83, 727-52. doi: 10.1146/annurev-biochem-060713-035456. PubMed PMID: 24580641; Kawamoto S A et al. *Design of triazole-stapled BCL9 alpha-helical peptides to target the beta-catenin/B-cell CLL/lymphoma 9 (BCL9) protein-protein interaction*. J Med Chem. (2012) 55, 1137-46. doi: 10.1021/jm201125d. PubMed PMID: 22196480; PMCID: 3286869; Madden M M et al. *Synthesis of cell-permeable stapled peptide dual inhibitors of the p53-Mdm2/Mdmx interactions via photoinduced cycloaddition*. Bioorg Med Chem Lett. (2011) 21, 1472-5. doi: 10.1016/j.bmcl.2011.01.004. PubMed PMID: 21277201; PMCID: 3057119; Moellering R E et al. *Direct inhibition of the NOTCH transcription factor complex*. Nature. (2009) 462, 182-8. doi: 10.1038/nature08543. PubMed PMID: 19907488; PMCID: 2951323; Liu T et al. *Synthesis and screening of a cyclic peptide library: discovery of small-molecule ligands against human prolactin receptor*. Bioorg Med Chem. (2009) 17, 1026-33. doi: 10.1016/j.bmc.2008.01.015. PubMed PMID: 18234500; PMCID: 2662701; Gavenonis J et al. *Comprehensive analysis of loops at protein-protein interfaces for macrocycle design*. Nat Chem Biol. (2014) 10, 716-22. doi: 10.1038/nchembio.1580. PubMed PMID: 25038791; PMCID: PMC4138238; Qian Z et al. *Targeting intracellular protein-protein interactions with cell-permeable cyclic peptides.* Curr Opin Chem Biol. (2017) 38, 80-6. doi: 10.1016/j.cbpa.2017.03.011. PubMed PMID: 28388463; PMCID: PMC5474178.) The size and polarity of cyclic peptides can fail to meet the criteria of Lipinski's "Rule of 5" for predicting drug-likeness. However, some cyclic peptides may exhibit the favorable ADME properties of small molecule drugs, including high passive cell permeability and oral bioavailability (BA). These exceptional cases include natural products such as cyclosporine A (CSA) and griselimycin. (Kling A et al. *Antibiotics. Targeting DnaN for tuberculosis therapy using novel griselimycins.* Science. (2015) 348, 1106-12. doi: 10.1126/science.aaa4690. PubMed PMID: 26045430.)

Achieving permeability in cyclic peptides is not straightforward. Although peptide cyclization can improve potency and proteolytic stability, simply removing the C- and N-termini alone is rarely sufficient for achieving good passive cell permeability. (Gao Y & Kodadek T. *Direct comparison of linear and macrocyclic compound libraries as a source of protein ligands.* ACS Combi Sci. (2015) 17, 190-5. doi: 10.1021/co500161c. PubMed PMID: 25623285; PMCID: PMC4356041; Sia S K et al. *Short constrained peptides that inhibit HIV-1 entry.* Proc Natl Acad Sci USA. (2002) 99, 14664-9. doi: 10.1073/pnas.232566599. PubMed PMID: 12417739; PMCID: PMC137476; Di L. *Strategic approaches to optimizing peptide ADME properties.* AAPS J. (2015) 17, 134-43. doi: 10.1208/s12248-014-9687-3. PubMed PMID: 25366889; PMCID: PMC4287298.) Backbone features such as stereochemistry, amide N-methylation, and the presence and position of non-proteinogenic residues such as peptoids, can influence passive membrane permeability by removing solvent-exposed NH groups, through direct capping, local steric occlusion, or by stabilizing intramolecular hydrogen bond (IMHB) networks. (Nielsen D S et al. *Orally Absorbed Cyclic Peptides.* Chem Rev. (2017) 117, 8094-128Epub 2017/05/26. doi: 10.1021/acs.chemrev.6b00838. PubMed PMID: 28541045; Dougherty P G et al. *Understanding Cell Penetration of Cyclic Peptides.* Chem Rev. (2019) 119, 10241-87Epub 2019/05/16. doi: 10.1021/acs.chemrev.9b00008. PubMed PMID: 31083977; PMCID: PMC6739158; Caron G et al. *Intramolecular hydrogen bonding. An opportunity for improved design in medicinal chemistry.* Med Res Rev. (2019) 39, 1707-29Epub 2019/01/20. doi: 10.1002/med.21562. PubMed PMID: 30659634.) With certain constraints dictated by conformation, side chain lipophilicity, and molecular weight, the chemical space that represents cyclic peptide scaffolds with favorable passive permeability is vast and largely unexplored. (Schwochert J et al. *Stereochemistry Balances Cell Permeability and Solubility in the Naturally Derived Phepropeptin Cyclic Peptides.* ACS Med Chem Lett. (2016) 7, 757-61. doi: 10.1021/acsmedchemlett.6b00100. PubMed PMID: 27563399; PMCID: PMC4983725; Hewitt W M et al. *Cell-permeable cyclic peptides from synthetic libraries inspired by natural products.* J Am Chem Soc. (2015) 137, 715-21. doi: 10.1021fja508766b. PubMed PMID: 25517352; Bockus A T et al. *Probing the Physicochemical Boundaries of Cell Permeability and Oral Bioavailability in Lipophilic Macrocycles Inspired by Natural Products.* J Med Chem. (2015) 58, 4581-9. doi: 10.1021/acs.jmedchem.5b00128. PubMed PMID: 25950816; Bockus A T et al. *Going out on a limb: Delineating the effects of beta-branching, N-methylation, and side chain size on the passive permeability, solubility, and flexibility of sanguinamide A analogs.* J Med Chem. (2015). doi: 10.1021/acs.jmedchem.5b00919. PubMed PMID: 26308180; White T et al. *On-resin N-methylation of cyclic peptides for discovery of orally bioavailable scaffolds.* Nat Chem Biol. (2011) 7, 810-7. doi: 10.1038/nchembio.664. PubMed PMID: WOS:000296381600011; Rezai T et al. *Conformational flexibility, internal hydrogen bonding, and passive membrane permeability: Successful in silico prediction of the relative permeabilities of cyclic peptides.* J Am Chem Soc. (2006) 128, 14073-80. doi: 10.1021/ja063076p. PubMed PMID: WOS:000241519600043; Wang C K et al. *Rational design and synthesis of an orally bioavailable peptide guided by NMR amide temperature coefficients.* Proc Natl Acad Sci USA. (2014) 111, 17504-9. doi: 10.1073/pnas.1417611111. PubMed PMID: 25416591; PMCID: 4267368; Furukawa A et al. *Passive Membrane Permeability in Cyclic Peptomer Scaffolds Is Robust to Extensive Variation in Side Chain Functionality and Backbone Geometry.* J Med Chem. (2016) 59, 9503-12. doi: 10.1021/acs.jmedchem.6b01246. PubMed PMID: WOS:000386641300017; Rand A et al. *Optimizing PK properties of cyclic peptides: the effect of side chain substitutions on permeability and clearance.* Medchemcomm. (2012) 3, 1282-9. doi: 10.1039/c2md20203d. PubMed PMID: WOS:000310423600012; Pye C R et al. *Nonclassical Size Dependence of Permeation Defines Bounds for Passive Adsorption of Large Drug Molecules.* J Med Chem. (2017) 60, 1665-72. doi: 10.1021/acs.jmedchem.6b01483. PubMed PMID: 28059508; PMCID: PMC5677520.) In extending these systems beyond the realm of natural products, diversity can be enhanced by introducing peptoid residues, for example, by using primary amines that are commercially available.

As molecular size increases, the potential to engage targets that lack deep clefts or pockets can improve. However, efforts to elucidate structure-permeability relationships in the "beyond the (Lipinski) Rule of 5" (bRo5) chemical space generally have been limited to small cyclic hexapeptide model systems. By contrast, the modification of a decapeptide molecule by the introduction of different combinations of N-Me-to-peptoid (Me being methyl) substitutions, in which the peptoid side chains were permuted to sample a range of lipophilicities, is discussed here. NMR analysis in solvents of varying polarity indicated significant differences in conformational rigidity in the two substitution patterns (Libraries A and B), which were consistent with their ADME and PK properties. These peptide-peptoid hybrids thus provide a new model system for studying and exploiting the impact of solvent-dependent conformational "chameleonicity" (and backbone rigidity) on permeability and other ADME and PK properties. For example, the approach presented herein allows for the design of such compounds and the compounds presented herein include cell permeable macrocycles with a molecular weight greater than 1000 Da (Dalton, g/mol) that are conformationally flexible.

EXAMPLES

The following examples provide descriptions of embodiments of the invention. Departures from the presented embodiments may be made that are within the scope of the invention. Modifications of the presented embodiments that remain within the scope of the invention may occur to a person skilled in the art. The specification, including the claims, should not be construed to unduly narrow the full scope of protection to which the invention is entitled.

Two cyclic peptomer scaffolds, Library A and Library B, were designed. The structure of a cyclic decapeptide 1 is shown in FIG. 1A. In the natural product gramicidin S, the solvent-exposed amides are capped with N-methyl groups. By having the solvent-exposed amides capped, the intramolecular hydrogen bonding network is preserved and the desolvation penalty associated with solvent-exposed N—H groups is eliminated. Compound 1 has a 4-residue extension in the central beta-strands, thus creating an extended array of transannular hydrogen bonds. Compound 1 can be abbreviated as

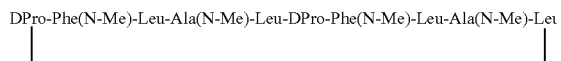

(in which DPro=D-proline, Phe=phenyalanine, Leu=leucine, Ala=alanine, and (N-Me) indicates a methyl (Me) substituted onto the nitrogen within the oligopeptide chain of the amino acid immediately to the left in the above sequence).

It is observed that peptoids can be introduced into a scaffold without abrogating permeability. The effect of N-methyl-to-peptoid substitutions on the physico-chemical and pharmokinetic (PK) properties of cyclic decapeptide 1 was tested. The method according to the invention encompasses generating further compounds by other substitutions. For example, commercially available primary amines can be used to diversify the peptoid positions.

In order to investigate the effect of NMe-to-peptoid substitutions on compound 1, we designed two libraries: Library A, replacing the two Phe-NMe residues in the opposing β-turns with peptoids (FIG. 1B), and Library B, replacing the two central Ala-NMe residues with peptoids (FIG. 1C). In each Library, the peptoid R-groups ($X^1$ and $X^2$) were selected from simple aliphatic and ether-containing amines (N1-N6, FIG. 1D); $X^3$ was selected, so that the amino acid (residue) of which $X^3$ was a part was rendered as either phenylalanine (Phe) or alanine (Ala); and the remaining residues were kept the same as those of compound 1, giving rise to 18 compounds for each Library. These compounds are summarized in Tables 4A and 4B. For example, the specific backbone elements, the pattern of stereochemistry, the presence and/or position of amide N-methyl, leucine, alanine, phenylalanine, and proline groups, and the presence and/or position of peptoid groups on the peptide/peptoid (for example, decapeptide-peptoid) ring can vary.

Throughout this text and in the Figures, unless otherwise indicated, the terms "log" and "Log" refer to the base-10 logarithm.

TABLE 4A

Figure 1B:
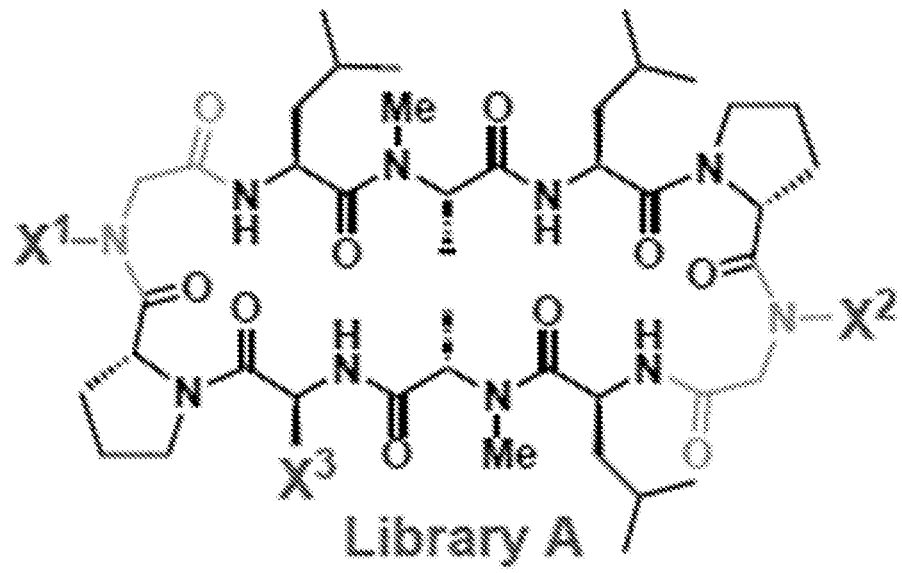
FIG. 1B. A design for a cyclic peptomers in Library A, showing positions (diversity positions) for substituents $X^1$, $X^2$, and $X^3$, is shown.
Figure 1C:
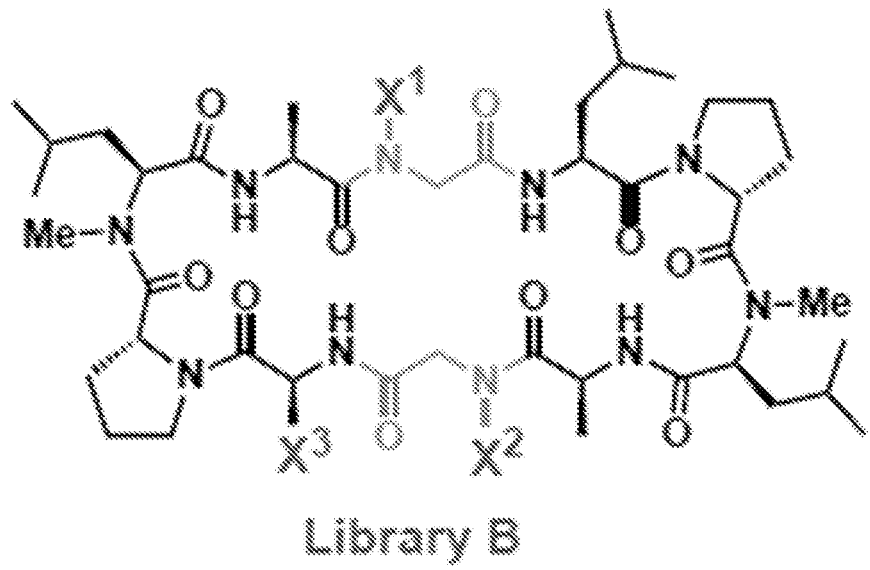
FIG. 1C. A design for a cyclic peptomers in Library B, showing positions (diversity positions) for substituents $X^1$, $X^2$, and $X^3$, is shown.
Figure 1D:
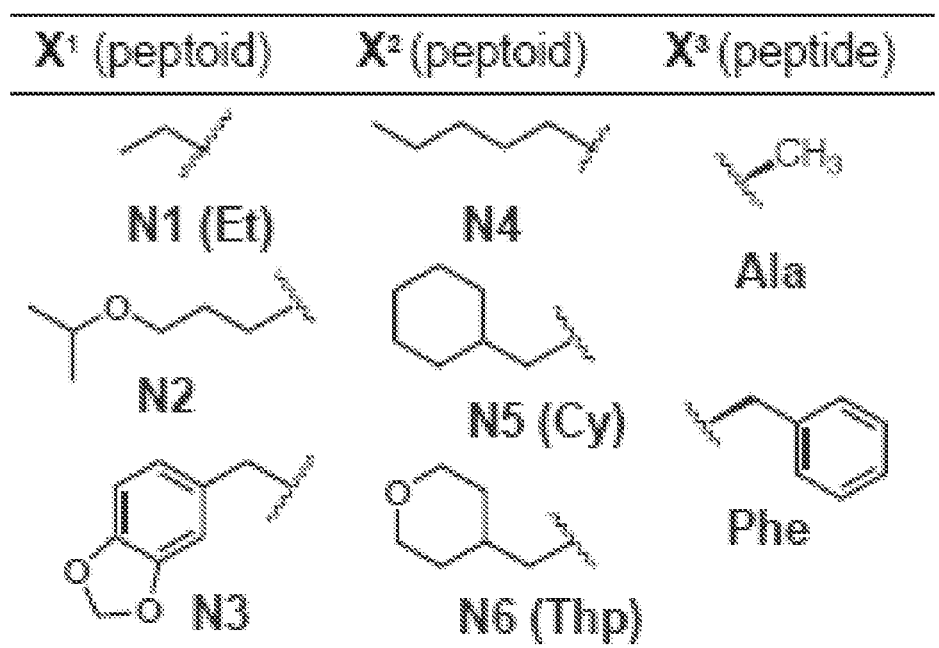
FIG. 1D. Peptoid ($X^1$ and $X^2$) and peptide ($X^3$) building blocks used in the synthesis of Libraries A and B are shown.

Compounds in Library A; the $X^1$, $X^2$, and $X^3$ substituents are at the positions shown in FIG. 1B; abbreviations for the $X^1$ and $X^2$ substituents are provided as N1 through N6.
Library A

| Compound Name | $X^1$ | $X^2$ | $X^3$ |
|---|---|---|---|
|  | ethyl (N1) | pentyl (N4) | methyl |
|  | ethyl (N1) | pentyl (N4) | benzyl |
|  | ethyl (N1) | cyclohexylmethyl (N5) | methyl |
| A08 | ethyl (N1) | cyclohexylmethyl (N5) | benzyl |
| A03 | ethyl (N1) | (oxan-4-yl)methyl (N6) | methyl |

TABLE 4A-continued

Compounds in Library A; the $X^1$, $X^2$, and $X^3$ substituents are at the positions shown in FIG. 1B; abbreviations for the $X^1$ and $X^2$ substituents are provided as N1 through N6.
Library A

| Compound Name | $X^1$ | $X^2$ | $X^3$ |
|---|---|---|---|
| A09 | ethyl (N1) | (oxan-4-yl)methyl (N6) | benzyl |
|  | 2-propoxy-3-propyl (N2) | pentyl (N4) | methyl |
|  | 2-propoxy-3-propyl (N2) | pentyl (N4) | benzyl |
|  | 2-propoxy-3-propyl (N2) | cyclohexylmethyl (N5) | methyl |
|  | 2-propoxy-3-propyl (N2) | cyclohexylmethyl (N5) | benzyl |
|  | 2-propoxy-3-propyl (N2) | (oxan-4-yl)methy (N6) | methyl |
|  | 2-propoxy-3-propyl (N2) | (oxan-4-yl)methy (N6) | benzyl |
|  | (1,3-benzodioxol-5-yl)-methyl (N3) | pentyl (N4) | methyl |
|  | (1,3-benzodioxol-5-yl)-methyl (N3) | pentyl (N4) | benzyl |
|  | (1,3-benzodioxol-5-yl)-methyl (N3) | cyclohexylmethyl (N5) | methyl |
|  | (1,3-benzodioxol-5-yl)-methyl (N3) | cyclohexylmethyl (N5) | benzyl |
|  | (1,3-benzodioxol-5-yl)-methyl (N3) | (oxan-4-yl)methyl (N6) | methyl |
|  | (1,3-benzodioxol-5-yl)-methyl (N3) | (oxan-4-yl)methyl (N6) | benzyl |

TABLE 4B

Compounds in Library B; the $X^1$, $X^2$, and $X^3$ substituents are at the positions shown in FIG. 1C.

| Compound Name | $X^1$ | $X^2$ | $X^3$ |
|---|---|---|---|
|  | ethyl (N1) | pentyl (N4) | methyl |
|  | ethyl (N1) | pentyl (N4) | benzyl |
|  | ethyl (N1) | cyclohexylmethyl (N5) | methyl |
| B08 | ethyl (N1) | cyclohexylmethyl (N5) | benzyl |
| B03 | ethyl (N1) | (oxan-4-yl)methyl (N6) | methyl |
| B09 | ethyl (N1) | (oxan-4-yl)methyl (N6) | benzyl |
|  | 2-propoxy-3-propyl (N2) | pentyl (N4) | methyl |
|  | 2-propoxy-3-propyl (N2) | pentyl (N4) | benzyl |
|  | 2-propoxy-3-propyl (N2) | cyclohexylmethyl (N5) | methyl |
|  | 2-propoxy-3-propyl (N2) | cyclohexylmethyl (N5) | benzyl |
|  | 2-propoxy-3-propyl (N2) | (oxan-4-yl)methyl (N6) | methyl |
|  | 2-propoxy-3-propyl (N2) | (oxan-4-yl)methyl (N6) | benzyl |
|  | (1,3-benzodioxol-5-yl)-methyl (N3) | pentyl (N4) | methyl |
|  | (1,3-benzodioxol-5-yl)-methyl (N3) | pentyl (N4) | benzyl |
|  | (1,3-benzodioxol-5-yl)-methyl (N3) | cyclohexylmethyl (N5) | methyl |
|  | (1,3-benzodioxol-5-yl)-methyl (N3) | cyclohexylmethyl (N5) | benzyl |
|  | (1,3-benzodioxol-5-yl)-methyl (N3) | (oxan-4-yl)methyl (N6) | methyl |
|  | (1,3-benzodioxol-5-yl)-methyl (N3) | (oxan-4-yl)methyl (N6) | benzyl |

Because permeability depends not only on scaffold geometry, but also on overall lipophilicity, the two Libraries were designed to sample a wide lipophilicity range, with calculated octanol/water partition coefficients (A Log P) ranging from 0.4 to 4.7. The peptoid R-groups and amino acid side chains were selected so that all library members had unique masses, allowing deconvolution of the mixtures by liquid chromatography-mass spectrometry (LCMS). (Hewitt W M et al. *Cell-Permeable Cyclic Peptides from Synthetic Libraries Inspired by Natural Products*. J Am Chem Soc. (2015) 137, 715-21. doi: 10.1021/ja508766b. PubMed PMID: BCI: BCI201500228766.) For example, the A log P of a compound can be at least −1, −0.5, 0, 0.4 (A03 and B03), 0.5, 1, 1.5, 1.9 (A09 and B09), 2, 2.5, 3, 3.5, 3.7 (A08 and B08), 4, 4.5, 4.7, 5, or 5.5 and/or can be at most −0.5, 0, 0.4 (A03 and B03), 0.5, 1, 1.5, 1.9 (A09 and B09), 2, 2.5, 3, 3.5, 3.7 (A08 and B08), 4, 4.5, 4.7, 5, 5.5, or 6.

Figure 2A:
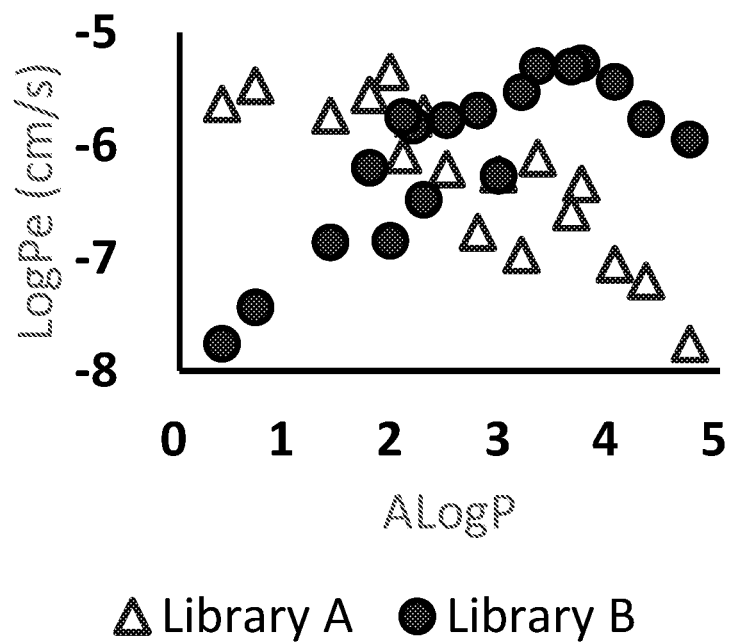
FIG. 2A. The graph shows the relationship between log of PAMPA effective permeability coefficient (Log Pe) and calculated (atomistic) octanol/water partition coefficient (A Log P) for compounds of Library A (hollow triangles) and compounds of Library B (solid circles).

Libraries A and B were synthesized separately as mixtures using solid phase split-pool peptide synthesis, incorporating peptoid side chains as primary amines using the submonomer method. (Zuckermann R N et al. *Efficient Method for the Preparation of Peptoids [Oligo(N-Substituted Glycines)] by Submonomer Solid-Phase Synthesis*. J Am Chem Soc. (1992) 114, 10646-7. doi: DOI 10.1021/ja00052a076. PubMed PMID: WOS:A1992KD71700076.) The libraries were cleaved, cyclized in solution, and roughly purified using solid phase extraction on C18 media. Parallel artificial membrane permeability assays (PAMPA) were used to measure passive permeabilities; PAMPA permeabilities within each library varied parabolically as a function of A Log P (FIG. 2A). The permeabilities of both Libraries A and B peaked at ~$10 \times 10^{-6}$ cm/s; however, although the permeability of Library A (FIG. 2A, hollow triangles) peaked at the polar end of the sampled lipophilicity range, with high (large) permeabilities found as low as A Log P=0.4, the permeability of Library B (solid circles) peaked at the higher end of the range, near A Log P~3.8.

A metric called lipophilic permeability efficiency (LPE), quantifies the efficiency with which a compound achieves passive membrane permeability at a given A Log P-defined lipophilicity. LPE is derived from the difference between the experimental decadiene-water partition coefficient, Log D(dec/w), and the calculated (atomistic) octanol/water partition coefficient, A Log P, and provides a lens through which to compare ADME properties, which is useful for bRo5 scaffolds. (Naylor M R et al. *Lipophilic Permeability Efficiency (LPE) reconciles the opposing roles of lipophilicity in membrane permeability and aqueous solubility*. J Med Chem. (2018), Epub 2018/11/06. doi: 10.1021/acs.jmedchem.8b01259. PubMed PMID: 30395703.) Because Log D(dec/w) is dependent on the degree to which hydrogen bond donors can be sequestered, either sterically or via intramolecular hydrogen bonds, LPE is highly sensitive to a compound's low-dielectric (small-dielectric), membrane-associated conformational ensemble. Log D(dec/w) reflects a molecule's net hydrogen bond acidity in its membrane-associated conformation (which pertains to permeability), and A Log P reflects a compound's minimum lipophilic character in the aqueous environment (which is correlated with aqueous solubility). For example, LPE can be defined as $$\text{LPE} = \text{Log } D(dec/w) - 1.06 A \text{ Log } P + 5.47$$

LPE can represent a scaffold's intrinsic membrane permeability by normalizing its membrane partitioning against its bulk lipophilicity.

Figure 2B:
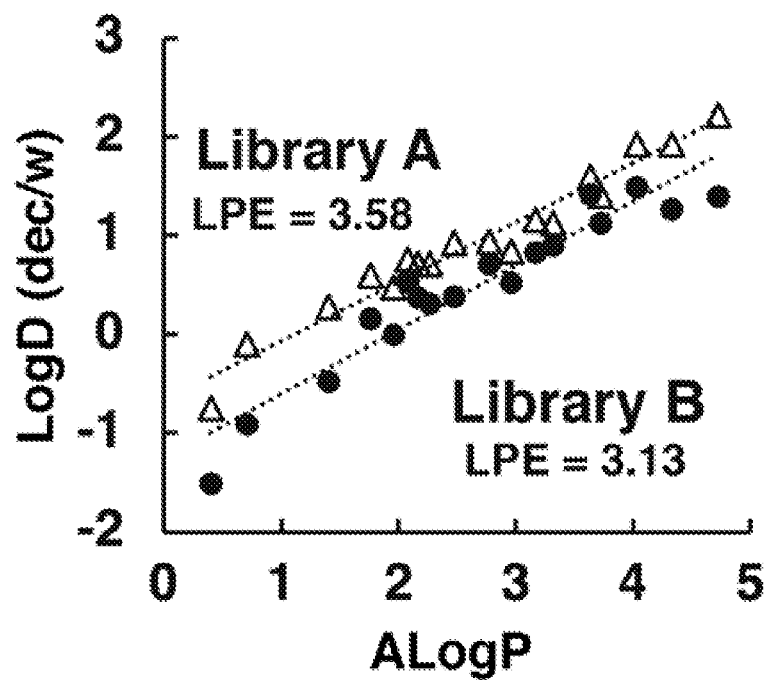
FIG. 2B. The graph shows the relationship between log of experimental hydrocarbon-water partition coefficient (Log D(dec/w)) at pH=7.4 and calculated (atomistic) octanol/water partition coefficient (A Log P) for compounds of Library A (hollow triangles) and compounds of Library B (solid circles).

Both aliphatic side chain variants on the same scaffold, as well as different scaffolds with the same degree of hydrogen bond donor (HBD) exposure, generally fall on the same 45° line in the plot of Log D(dec/w) vs. A Log P, resulting in similar LPE values (FIG. 2B). The average LPE values for Libraries A and B are also similar, 3.58 (s.d.=0.57) and 3.13 (s.d.=0.55), respectively, suggesting that both scaffolds achieve similar degrees of IMHB in low dielectric environments (FIG. 2B).

Figure 2C:
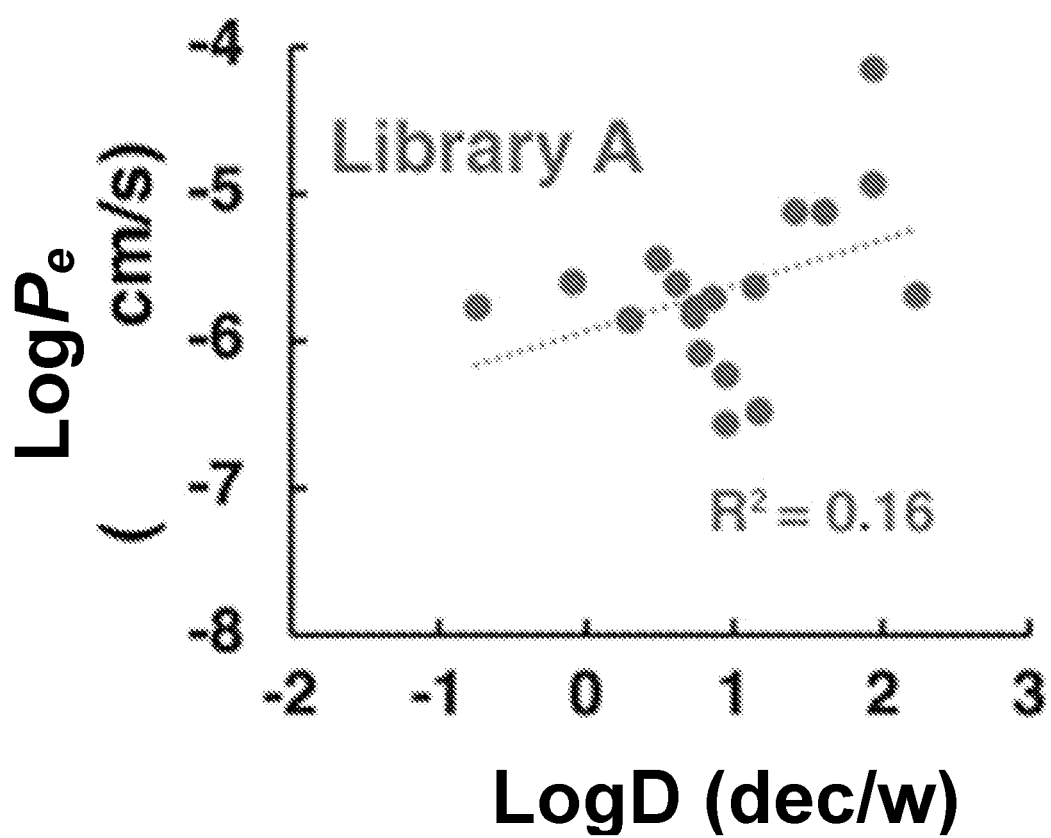
FIG. 2C. The graph shows the relationship between log of PAMPA effective permeability coefficient (Log Pe) and log of experimental hydrocarbon-water partition coefficient (Log D(dec/w) for compounds of Library A.
Figure 2D:
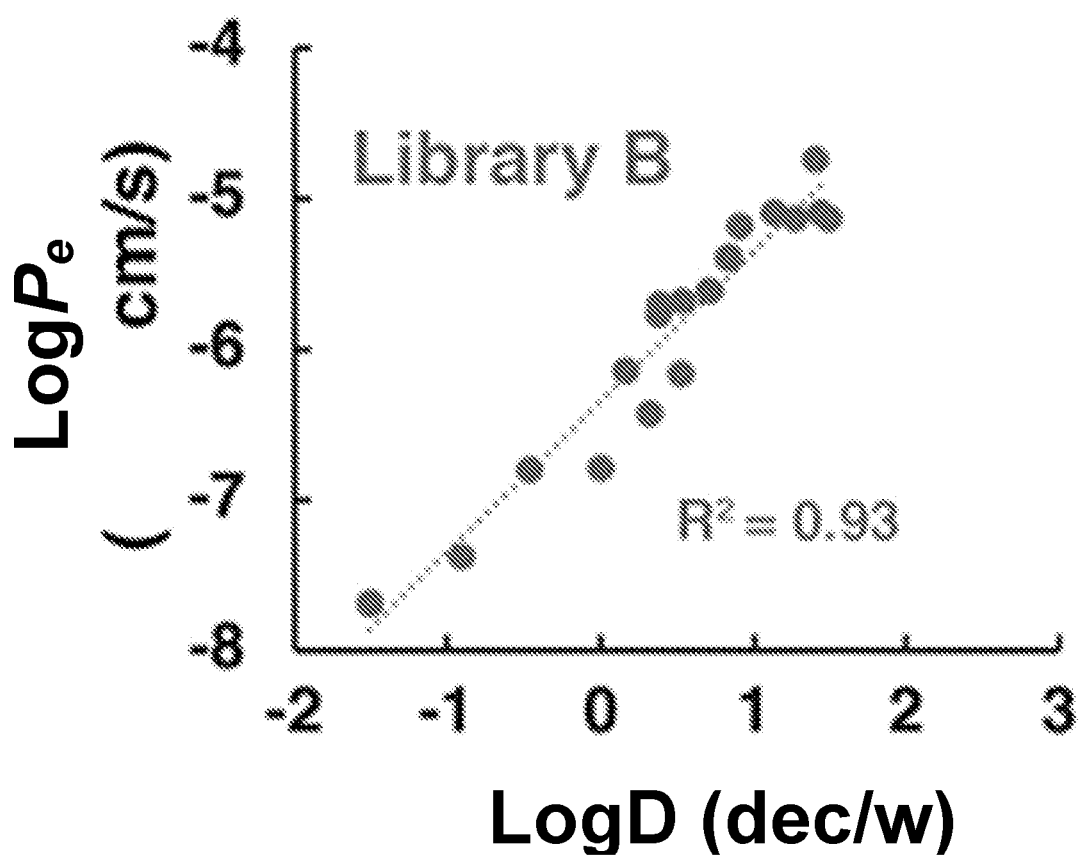
FIG. 2D. The graph shows the relationship between log of PAMPA effective permeability coefficient (Log Pe) and log of experimental hydrocarbon-water partition coefficient (Log D(dec/w)) for compounds of Library B.

On the ascending (polar) portion of the A Log P vs. permeability curve, the correlation between Log D(dec/w) and membrane permeability is high, whereas the correlation breaks down on the descending portion of the curve where poor (small) solubility begins to dominate the behavior (FIG. 2A). This observation underscores the fact that distinct physical phenomena govern the relationship between lipophilicity and permeability in the soluble versus insoluble regimes, with the correlation between permeability and Log D(dec/w) being high (strong) only in the soluble regime. Consistent with these observations, the correlations between Log D(dec/w) and Log $P_e$ are significantly different for Libraries A and B (compare FIG. 2C with FIG. 2D). For Library A, any correlation between Log D(dec/w) and Log $P_e$ is negligible (FIG. 2C) ($R^2$=0.16), whereas for Library B the correlation is strong (FIG. 2D) ($R^2$=0.93). These data are consistent with plots of Log Pe versus A Log P for Libraries A and B, in which most of the Library B compounds fall on the polar, ascending part of the curve, whereas nearly every Library A compound falls in the descending, insoluble part (FIG. 2A). Furthermore, most Library B compounds showed good recovery in PAMPA even up to A Log P=4 (FIG. 2A), whereas recoveries for Library A fell off significantly above A Log P~2; recovery being defined as the final total compound mass in the PAMPA donor and receiver compartments over the initial compound mass in the donor compartment. These observations, and the 2 Log unit separation between the A Log P-versus-permeability curves for Libraries A and B, suggest that the position of the peptoid substituents confers distinct physical properties to the scaffold of Library A and the scaffold of Library B.

Figure 4A:
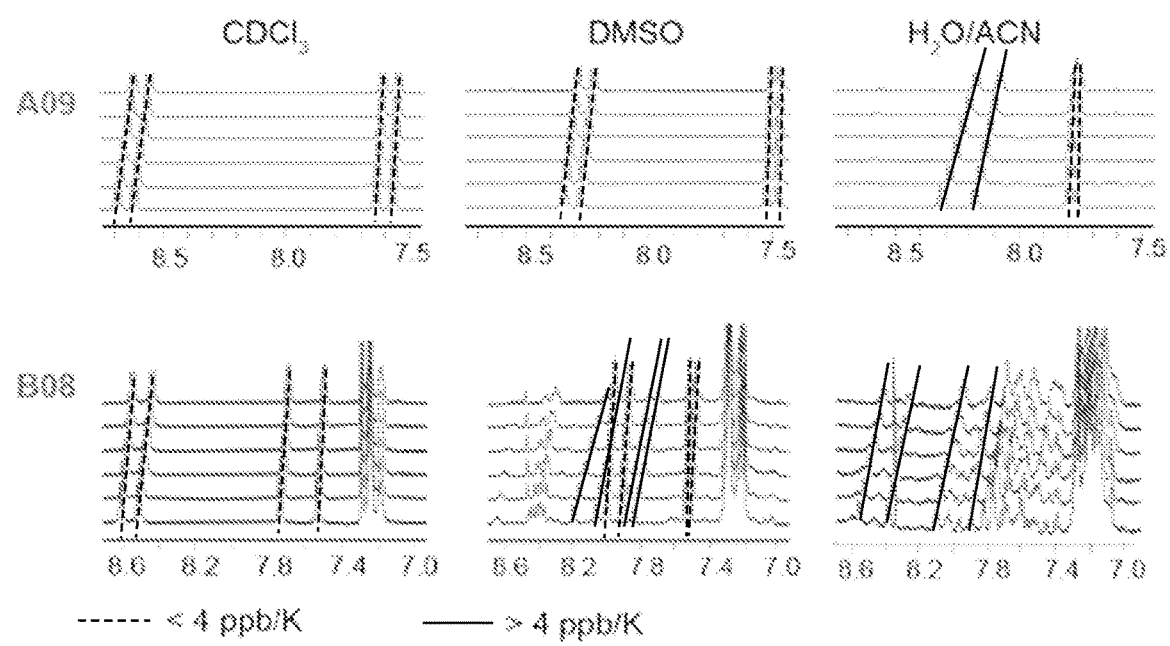
FIG. 4A. Shown are nuclear magnetic resonance (NMR) temperature shifts for compounds A09 and B08 in each of the solvents deuterated chloroform ($CDCl_3$), dimethylsulfoxide (DMSO), and a water/acetonitrile mixture ($H_2O$/ACN). Dashed lines across curves indicate a shift of less than 4 ppb/K; solid lines across curves indicate a shift of greater than 4 ppb/K.

In order to test whether Libraries A and B, like an all-peptide scaffold corresponding to each of them, sequester their backbone NH groups in IMHB, the most permeable representatives of each scaffold (Library), A09 and B08, were synthesized, and their NMR temperature shifts in solvents of varying polarity were investigated. In chloroform ($CDCl_3$), A09 and B08 showed equally low temperature coefficients for all four amide NH groups, consistent with the similarity in their LPE values (FIG. 4A). However, the two scaffolds behaved very differently in polar solvents. In both dimethylsulfoxide (DMSO) and a water/acetonitrile mixture ($H_2O$/ACN), A09 maintained its conformational stability, showing only a modest increase in NH temperature shift coefficients with increasing polarity. In contrast, the amide signals of B08 split into multiple families in DMSO, splitting even further in $H_2O$/ACN. The NMR spectra thus indicate that in both low and high-dielectric environments, A09 is almost completely locked into its "closed" conformer. In contrast, although B08 adopts a fully closed conformation in $CDCl_3$ (deuterated chloroform), it adopts an increasingly complex ensemble of more open species (conformational heterogeneity) as polarity increases. Scaffold (Library) A thus behaves more like a corresponding all-peptide scaffold, supported by molecular dynamics studies showing compound 1 to be rigid in both chloroform and water. (Witek J et al. *Rationalization of the Membrane Permeability Differences in a Series of Analogue Cyclic Decapeptides*. J Chem Inf Model. (2019) 59, 294-308Epub 2018/11/21. doi: 10.1021/acs.jcim.8b00485. PubMed PMID: 30457855.) In contrast, the behavior of scaffold (Library) B is more like that of cyclosporine A (CSA), a "chameleonic" cyclic peptide that, although rigid and closed in chloroform, adopts multiple, open conformers in water. (el Tayar N et al. *Solvent-dependent conformation and hydrogen-bonding capacity of cyclosporin A: evidence from partition coefficients and molecular dynamics simulations.* J Med Chem. (1993) 36, 3757-64. PubMed PMID: 8254605; Witek J et al. *Interconversion Rates between Conformational States as Rationale for the Membrane Permeability of Cyclosporines.* Chemphyschem. (2017) 18, 3309-14. doi: 10.1002/cphc.201700995. PubMed PMID: 28921848; Witek J et al. *Kinetic Models of Cyclosporin A in Polar and Apolar Environments Reveal Multiple Congruent Conformational States.* J Chem Inf Model. (2016) 56, 1547-62. doi: 10.1021/acs.jcim.6b00251. PubMed PMID: 27387150; Kessler H et al. *Complexation and medium effects on the conformation of cyclosporin A studied by NMR spectroscopy and molecular dynamics calculations.* Biochem Pharmacol. (1990) 40, 169-73. PubMed PMID: 2164815; Wang C K et al. *Conformational Flexibility Is a Determinant of Permeability for Cyclosporin.* J Phys Chem B. (2018). doi: 10.1021/acs.jpcb.7b12419. PubMed PMID: 29400464.)

Figure 4B:
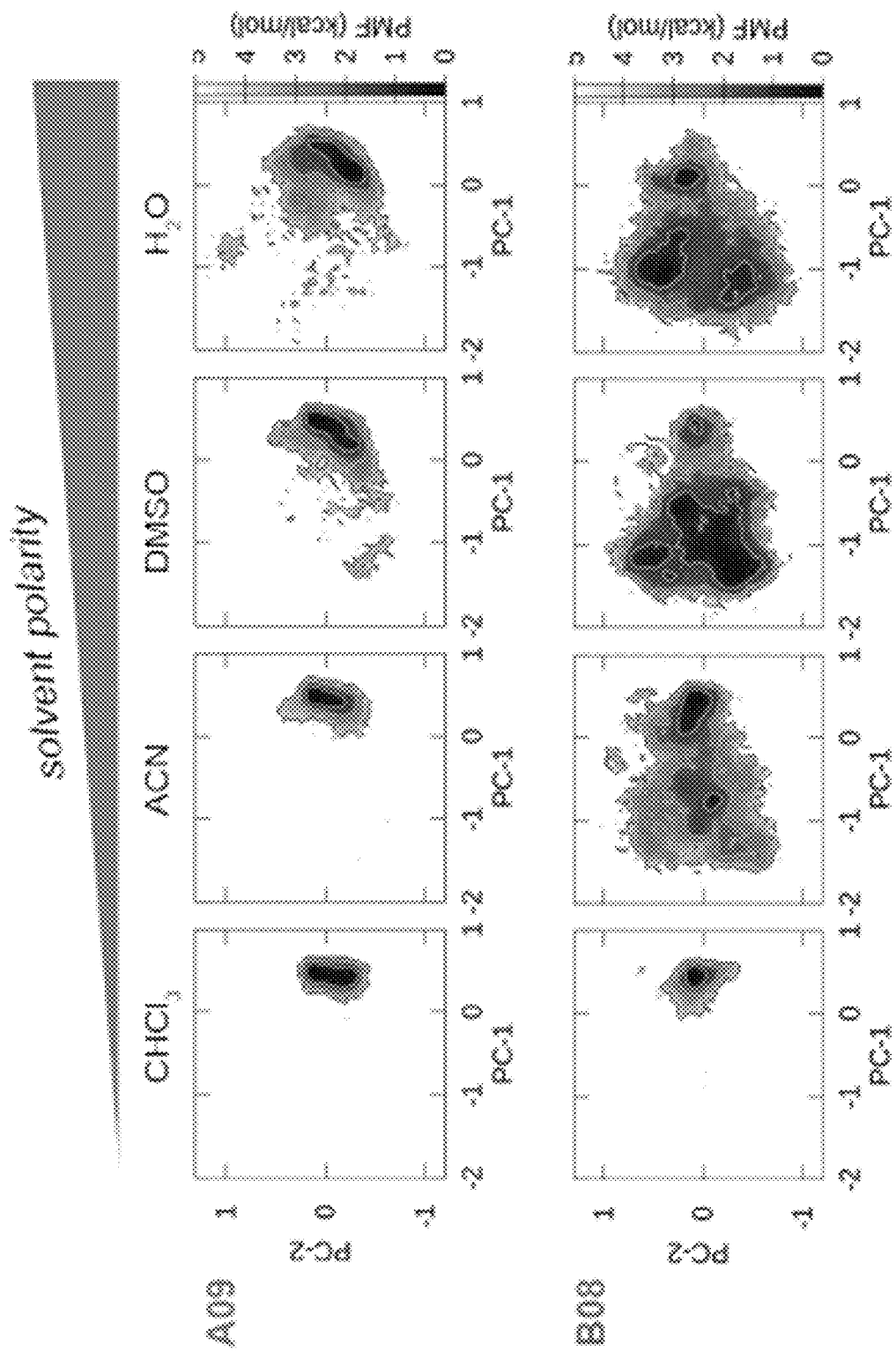
FIG. 4B. Multicanonical molecular dynamics (MCMD) results for compounds A09 and B08 are shown as the principle components PC-1 and PC-2 of the conformational ensembles of A09 and B08 in solvents of increasing polarity ($CHCl_3$ (chloroform), ACN (acetonitrile), DMSO (dimethylsulfoxide), and $H_2O$ (water)).
Figure 4C:
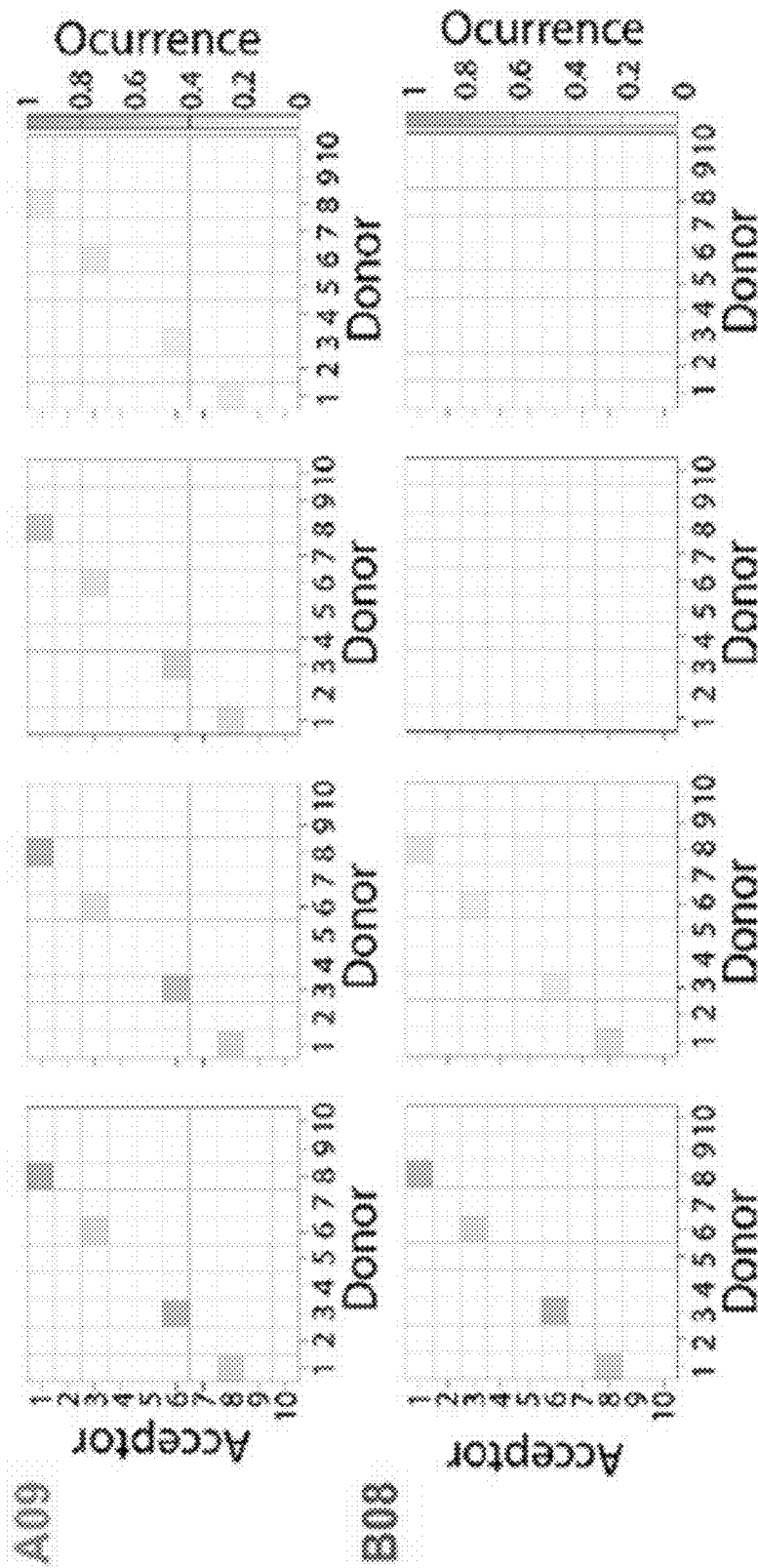
FIG. 4C. MCMD results for compounds A09 and B08 are shown as a hydrogen bond plot showing percentage of the ensemble with the hydrogen bonds shown (the primary pattern visible indicates the canonical cross-beta transannular hydrogen bonds found in the parent structure).

In order to test the hypothesis that scaffolds (Libraries) A and B have different conformational stabilities and that the ensemble observed for B08 in higher dielectric solvents represents a variety of more open conformational states, their conformations using multicanonical molecular dynamics (MD) (MCMD) simulations were investigated. (Nakajima N et al. *Multicanonical ensemble generated by molecular dynamics simulation for enhanced conformational sampling of peptides.* J Phys Chem B. (1997) 101, 817-24. PubMed PMID: WOS:A1997WL11000018.) MCMD provides a useful method for sampling conformational space in cyclic peptides and predicting properties based on the resulting ensembles. (Ono S et al. *Conformation and Permeability: Cyclic Hexapeptide Diastereomers.* J Chem Inf Model. (2019) 59, 2952-63Epub 2019/05/03. doi: 10.1021/acs.jcim.9b00217. PubMed PMID: 31042375.) MCMD simulations of A09 and B08 in explicit solvents ranging in polarity from chloroform to water showed that both compounds adopt compact folds in chloroform. However, although A09 maintained its cross-beta structure in water, the hydrogen bond network of B08 became increasingly destabilized with increasing solvent polarity (FIG. 4B). The scaffolds representing Libraries A and B therefore provide a means of comparing chameleonic and non-chameleonic compounds in the "beyond the (Lipinski) Rule of 5" (bRo5) macrocycle space using compounds that otherwise share identical compositions and calculated (2-D) properties.

Figure 3A:
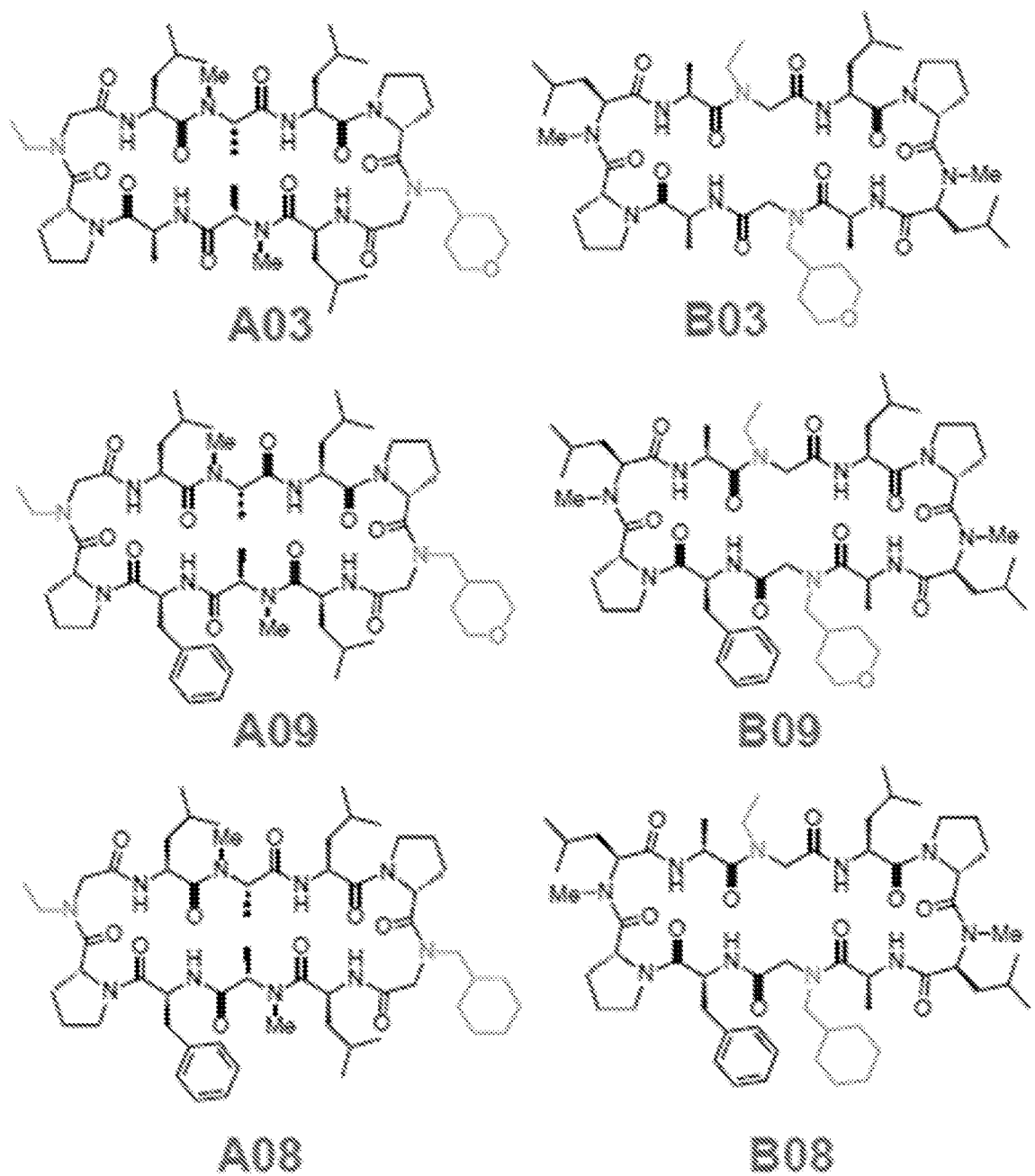
FIG. 3A. The structures of compounds A03, A09, and A08 of Library A and the structures of compounds B03, B09, and B08 of Library B are shown; these compounds were synthesized and tested individually.
Figure 3B:
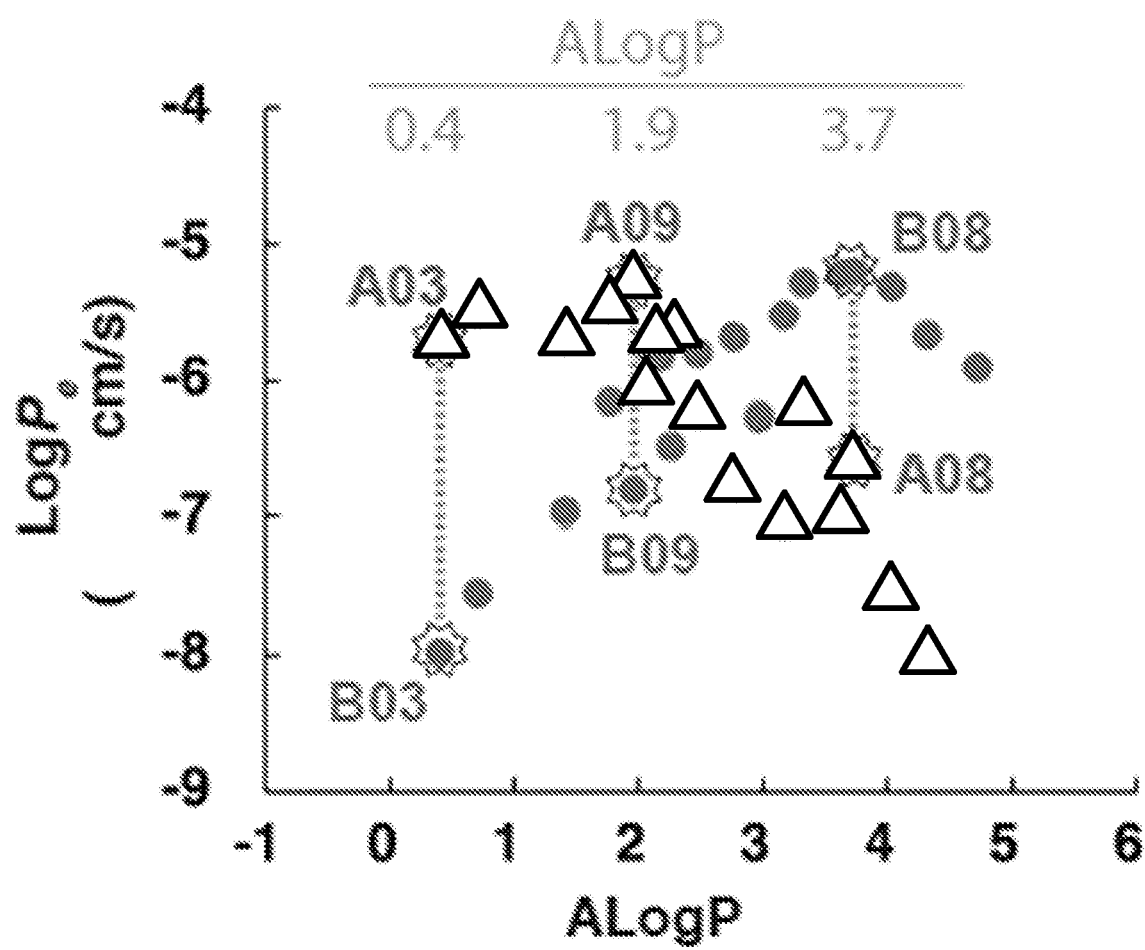
FIG. 3B. The graph shows the relationship between log of PAMPA effective permeability coefficient (Log $P_e$) and calculated (atomistic) octanol/water partition coefficient (A Log P) for compounds of Library A (hollow triangles) and compounds of Library B (solid circles). Compounds A03 and B03 are a pair of isomers; compounds A09 and B09 are a pair of isomers; and compounds A08 and B08 are a pair of isomers; these three pairs of isomers were selected to have a range of lipophilicities from the calculated (atomistic) octanol/water partition coefficient (A Log P) (A Log P=0.4, 1.9, and 3.7).
Figure 5:
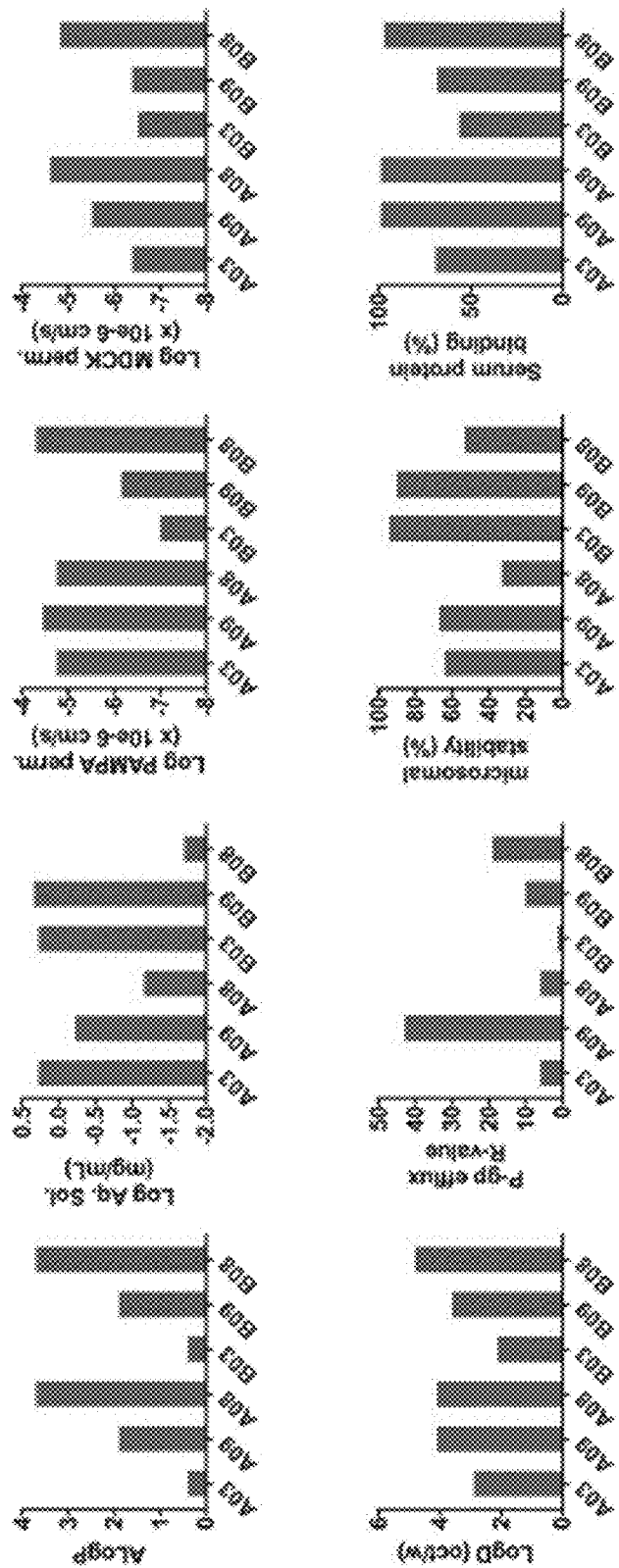
FIG. 5. Graphs of calculated (atomistic) octanol/water partition coefficient (plotted as the base-10 logarithm) (A Log P), aqueous solubility (plotted as the Log) (Log Aq. Sol.), parallel artificial membrane permeability assays (PAMPA) permeability (plotted as the Log), MDCK permeability (plotted as the Log), experimental octanol/water partition coefficient (plotted as the Log) (Log D (oct/w)), P-gp efflux ratios, microsomal stability, and serum protein binding of compounds in Library A (A03, A09, and A08) and in Library B (B03, B09, and B08) (in vitro ADME assays) (see Table 1 for values and comments on each assay).

To further elucidate the structure-property relationships of the two scaffolds, several representatives from each Library were synthesized as pure compounds. That is, three matched compound pairs that span a wide lipophilicity range were synthesized: compounds A03 and B03 (A Log P=0.4); compounds A09 and B09 (A Log P=1.9); and compounds A08 and B08 (A Log P=3.7) (FIG. 3A & Table 1). FIG. 3B presents the same data that are shown in FIG. 2A, that is, the data obtained for the compounds in the Library A and the Library B mixtures, but indicates the compounds that were also synthesized as pure compounds. The members of each pair have the same set of side chains and differ only in the position of the peptoid residues. For each of these six pure compounds, calculated (atomistic) octanol/water partition coefficient (A Log P), aqueous solubility (Aq. Sol), PAMPA and MDCK permeabilities, experimental octanol/water partition coefficient (Log D (oct/w)), P-gp efflux ratios, microsomal stability, and serum protein binding were determined (Table 1 and FIG. 5). The behavior of these pure compounds was, for the most part, similar to their behavior in the original Library mixtures, with some differences. As discussed below, for these pure compounds PAMPA permeabilities were obtained under a "sink" condition. For the most part, the measured PAMPA permeability value obtained under the "sink" condition for a compound in the pure form was greater than the measured PAMPA permeability value obtained under the standard condition for the compound in the mixture for the Library of which it was a part. However, as discussed below, for compounds in a given Library, the trend in PAMPA permeability values obtained under the "sink" condition for the pure compounds with the calculated (atomistic) octanol/water partition coefficient (A Log P) was similar to the trend in PAMPA permeability values obtained under the standard condition for those compounds as part of the Library mixture with A Log P. Aqueous solubility tracked approximately with A Log P for both scaffolds (Libraries): the compounds of the most polar pair (A03 and B03) were soluble (1900 and 1900 µg/mL, respectively), whereas compounds of the most lipophilic pair (A08 and B08) were about two orders of magnitude less soluble (70 and 20 µg/mL, respectively). For the pair in the middle, at A Log P=1.9, the chameleonic scaffold (B09) was nearly 4-fold more water-soluble than its rigid counterpart (A09) (2200 and 600 µg/mL, respectively).

For example, the aqueous solubility of a compound (or minimum aqueous solubility) can be at least 0.0003, 0.001, 0.003, 0.007, 0.01, 0.02, 0.03, 0.07, 0.1, 0.2, 0.3, 0.6, 1, 1.9, 2.2, 3, 5, or 10 mg/mL and/or at most 0.001, 0.003, 0.007, 0.01, 0.02, 0.03, 0.07, 0.1, 0.2, 0.3, 0.6, 1, 1.9, 2.2, 3, 5, 10, or 30 mg/mL. For example, the permeability of a compound (Log Pe) can be at least $0.001 \times 10^{-6}$, $0.003 \times 10^{-6}$, $0.01 \times 10^{-6}$, $0.03 \times 10^{-6}$, $0.1 \times 10^{-6}$, $0.2 \times 10^{-6}$, $0.3 \times 10^{-6}$, $0.5 \times 10^{-6}$, $1 \times 10^{-6}$, $2 \times 10^{-6}$, $3 \times 10^{-6}$, $5 \times 10^{-6}$, $10 \times 10^{-6}$, $30 \times 10^{-6}$, $100 \times 10^{-6}$, or $300 \times 10^{-6}$ cm/s and/or at most $0.003 \times 10^{-6}$, $0.01 \times 10^{-6}$, $0.03 \times 10^{-6}$, $0.1 \times 10^{-6}$, $0.2 \times 10^{-6}$, $0.3 \times 10^{-6}$, $0.5 \times 10^{-6}$, $1 \times 10^{-6}$, $2 \times 10^{-6}$, $3 \times 10^{-6}$, $5 \times 10^{-6}$, $10 \times 10^{-6}$, $30 \times 10^{-6}$, $100 \times 10^{-6}$, $300 \times 10^{-6}$, or $1000 \times 10^{-6}$ cm/s. For example, the Log D of a compound can be at least −3, −2.5, −2, −1.5, −1, −0.5, 0, 0.5, 1, 1.5, 2, 2.5, 3, 3.5, 4, 4.5, 5, or 5.5 and/or at most −2.5, −2, −1.5, −1, −0.5, 0, 0.5, 1, 1.5, 2, 2.5, 3, 3.5, 4, 4.5, 5, 5.5, or 6.

TABLE 1

| Lib | Cpd | $X^1$ | $X^2$ | $X^3$ | ALogP | Aq. Sol. (mg/mL)[1] | LogD (oct/w)[2] | PAMPA Perm. ($\times 10^{-6}$ cm/s) | MDCK Perm. ($\times 10^{-6}$ cm/s) | P-gp R-value[3] | Microsomal Stability (%)[4] | Serum Protein Binding (%)[5] |
|---|---|---|---|---|---|---|---|---|---|---|---|---|
| A | A03 | Et | Thp | Ala | 0.4 | 1.900 | 2.9 | 17.2 | 0.4 | 6.4 | 64 | 69 |
| A | A09 | Et | Thp | Phe | 1.9 | 0.640 | >4.1 | 35.7 | 3.1 | 46.9 | 67 | 98 |
| A | A08 | Et | Cy | Phe | 3.7 | 0.0068 | >4.4 | 18.8 | 24.7 | 8.5[6] | 33 | >99.8 |
| B | B03 | Et | Thp | Ala | 0.4 | 1.900 | 2.1 | >10.1 | 0.3 | 1.4 | 94 | 57 |
| B | B09 | Et | Thp | Phe | 1.9 | 2.200 | 3.6 | 1.4 | 0.4 | 10.3 | 90 | 68 |

TABLE 1-continued

| Lib | Cpd | X[1] | X[2] | X[3] | ALogP | Aq. Sol. (mg/mL)[1] | LogD (oct/w)[2] | PAMPA Perm. (×10⁻⁶ cm/s) | MDCK Perm. (×10⁻⁶ cm/s) | P-gp R-value[3] | Microsomal Stability (%)[4] | Serum Protein Binding (%)[5] |
|---|---|---|---|---|---|---|---|---|---|---|---|---|
| B | B08 | Et | Cy  | Phe | 3.7 | 0.210 | >4.8 | >50 | 15.3 | 19.2 | 53 | 97 |
| A | A03 | Et | Thp | Ala | 0.4 | 1.900 | 2.9  | 18  | 0.4  | 6    | 64 | 69 |
| A | A09 | Et | Thp | Phe | 1.9 | 0.600 | 4.1  | 35  | 3.1  | 43   | 67 | 99 |
| A | A08 | Et | Cy  | Phe | 3.7 | 0.070 | 4.1  | 18  | 25   | 6[6] | 33 | 99 |
| B | B03 | Et | Thp | Ala | 0.4 | 1.900 | 2.1  | 0.1 | 0.3  | 1.4  | 94 | 56 |
| B | B09 | Et | Thp | Phe | 1.9 | 2.200 | 3.6  | 0.7 | 0.4  | 10   | 90 | 68 |
| B | B08 | Et | Cy  | Phe | 3.7 | 0.020 | 4.8  | 50  | 15   | 19   | 53 | 97 |

[1]Japanese Pharmacopoeia Second Fluid (pH 6.8)
[2]pH 7.4
[3]The compound with R value ≥1.5 could be a substrate of P-gp
[4]Remaining rate of the compounds after 30 min of incubation with pooled liver microsomes (0.1 mg/mL, rats)
[5]Bound fractions (%) in rat plasma
[6]A08 was tested at 1 μM while the others were tested at 10 μM PAMPA permeability studies on these six pure compounds were performed initially under the same conditions as those used in the original library screen, using a concentration of 1 μM in the donor well based on the estimated concentration of each compound in the original library. Under these conditions, no compound was observed in the acceptor well for any of the six compounds, yielding $P_{app}$ values of <0.01×10⁻⁶ cm/s, in contrast to the permeabilities observed in the original mixtures. When the donor well concentrations were increased to 20 μM, some membrane transport was observed for A09 and B08, the most permeable library members, although the calculated $P_{app}$ values were still lower than those measured when each compound was in the mixture for its respective Library. Without being bound by theory, it was hypothesized that the pure compounds were precipitating in the donor well or adhering to the walls of the apparatus, and that as mixtures they could act as pseudo-detergents (or mutual blocking agents) to help prevent escape from solution (such as through aggregation or adsorption). Therefore, the PAMPA permeabilities of the pure compounds using detergents in the donor and acceptor wells as "sink" conditions were re-investigated. Using these conditions, the permeability trends were similar to those observed in the Libraries. At the polar end of the continuum, A03 (18×10⁻⁶ cm/s) was more permeable than B03 (<0.1 ×10⁻⁶ cm/s), whereas at the lipophilic end this trend was reversed, with B08 (>50×10⁻⁶ cm/s) being more permeable than A08 (18×10⁻⁶ cm/s). The PAMPA permeabilities of the scaffold A compounds were high (large) across the entire A Log P range, whereas the permeabilities of scaffold B compounds trended upward (greater) along with A Log P.

Permeabilities were also measured in a Madin-Darby canine kidney (MDCK) permeability assay, in which the passage of the compound through a semipermeable membrane coated with MDCK cells is measured. The MDCK permeability trends exhibited some differences from the permeability trends observed from the PAMPA studies. All but the most polar compounds had high P-gp efflux ratios, thus complicating interpretation of the cell permeability data. For both scaffolds, increasing A Log P led to lower microsomal stability and higher plasma protein binding, although compounds from the more flexible Library B scaffold were, on average, more metabolically stable and less protein bound than compounds from the rigid Library A scaffold.

Based on their permeabilities in PAMPA and MDCK cells, the in vivo pharmacokinetics of 5 of these 6 pure compound library members were investigated (B03 was not included in the oral PK study, because of its low (small) PAMPA and MDCK permeabilities). When administered orally to mice, absorption was low for all 5 compounds (Table 2); this result was consistent with the compounds' high efflux ratios and generally poor microsomal stabilities. To test whether metabolism and efflux were the main factors contributing to the low oral bioavailability (BA), mice were pretreated with either the CYP inhibitor 1-aminoazabenztriazole (ABT), the P-gp inhibitor elacridar (GF120918), or a combination of both the CYP and P-gp inhibitors. Both CYP and P-gp inhibition significantly increased oral bioavailability for all 5 compounds, and for three of the compounds the two inhibitors had a synergistic effect. Combining the inhibitors also produced oral bioavailabilities that reflected the compounds' relative PAMPA permeabilities. For A03, BA also increased as a function of the oral dosage, with oral BA increasing from 1% to 50% (when the oral dosage was increased from 3 to 200 mg/kg) even without CYP or P-gp inhibition (Table 3).

TABLE 2

Oral bioavailabilities in mice, with no inhibitors, pretreatment with CYP inhibitor, pretreatment with P-gp inhibitor, or pretreatment with CYP and P-gp inhibitors.

| Cpd. | No inhib. (%) | +CYP inhib.[a] (%) | +P-gp inhib.[b] (%) | +CYP inhib.[a] +P-gp inhib.[b] (%) |
|---|---|---|---|---|
| A03 | 1    | 2    | 4  | 39    |
| A09 | 2    | 5    | 22 | 105[c] |
| A08 | 5    | 31   | 7  | 59    |
| B03 | —    | —    | —  | —     |
| B09 | 0.7  | 1.5  | 3  | 14    |
| B08 | 6    | 148[c] | 13 | 101[c] |

[a]1-aminobenztriazole, cytochrome P450 (CYP) inhibitor.
[b]GF120918, P-glycoprotein (P-gp) inhibitor.
[c]The value >100% was caused by the uncertainty of extrapolation after the last time point.

TABLE 3

Oral bioavailabilities in mouse of A03 as a function of oral dose.

| Oral dose (mg/kg) | 3 | 30 | 100 | 200 |
|---|---|---|---|---|
| BA (%) | 0.99 | 11.5 | 22.1 | 49.8 |

Based on area under curve (AUC) at 1 mg/kg intravenous (IV) dose.

For the most lipophilic compounds, A08 and B08, inhibition of CYP-mediated metabolism caused a greater increase in oral BA than did inhibition of P-gp efflux. For the more polar compounds (A03, A09, and B09), P-gp inhibition had a more significant effect on oral BA, and the synergy between CYP and P-gp inhibition was also greater than for the more lipophilic compounds. Consistent with their observed PAMPA permeabilities, the oral BAs of the scaffold (Library) A compounds (with CYP and P-gp inhibition) were remarkably high (large) across the entire A Log P range, with a maximum BA of >100% for A09 in the middle of the range. Also consistent with their permeability trends, for scaffold (Library) B compounds the maximum oral BA (also >100%) was observed at the high (large) end of the A Log P range (compound B08). Thus, to a large degree the oral bioavailabilies of these compounds reflected their in vitro ADME behavior when efflux and metabolism were factored out through the use of inhibitors.

Libraries A and B represent isomeric scaffolds, in which selected amino acid residues from a parent cyclic decapeptide were substituted by peptoid residues. Peptoid side chains can be incorporated during synthesis as primary amines, thus providing access to much greater structural diversity than is accessible using commercially available, Fmoc-protected amino acids. The effect of specific peptoid substitutions on the parent compound's ADME and pharmacokinetic properties, including membrane permeability, aqueous solubility, metabolism, protein binding, and oral bioavailability, were evaluated. Solubility and membrane permeability are impacted by the additive effects of side chain lipophilicity (as captured by A Log P), as well as by more subtle effects governed by scaffold geometry and conformation (as captured experimentally by Log D(dec/w)). In order to tease apart these effects for cyclic decapeptide-peptoid hybrids, Libraries based on two scaffolds, A and B, defined by the relative placement of two peptoid residues within the cross-beta structure of the macrocycle, were synthesized. Each Library was comprised of side chain variants whose additive lipophilicities spanned an A Log P range of approximately 5 Log units. A single substitution of an ether oxygen with a methylene group (i.e., the difference between A09 and A08, and between B09 and B08) leads to a 2 Log unit increase in A Log P, highlighting the large effect that a single-atom substitution can have on the calculated properties of a large macrocyclic peptide-peptoid.

The location of the peptoid residues had a profound effect on the solvent-dependent conformational behavior of these two scaffolds. While peptoid substitutions at the i+2 positions of the two β-turns (Library A) retained the conformational stability of the parent compound in both low- and high-dielectric (small- and large-dielectric) media, peptoid substitutions in the middle of each β-strand (Library B) destabilized the scaffold's conformation, resulting in a solvent-dependent conformational heterogeneity. This difference in "chameleonicity" between scaffolds (Libraries) A and B, as observed by NMR temperature shifts and corroborated by MD simulations, is consistent with the large displacement in the permeability vs. A Log P curves of Libraries A and B along the A Log P axis. Scaffold A, which even in water exists primarily in the hydrogen-bonded, cross-β conformation, achieves peak permeability at a relatively low (small) calculated lipophilicity (below A Log P~2). Scaffold B, in contrast, requires a higher (larger) calculated lipophilicity (A Log P~4) to reach the same permeability. However, the relatively small difference between experimental Log D(dec/w) values among the A Log P-matched pairs for scaffolds A and B suggests that the rightward shift in the A Log P-vs.-permeability curve of scaffold B cannot be explained simply as the energetic penalty for adopting its membrane-associated conformation compared to the more rigid scaffold A. Without being bound by theory, the relatively small difference in Log D(dec/w) values between scaffold A and B compounds of the same A Log P (and the correspondingly small difference in LPE between the two scaffolds) suggests that the thermodynamics of membrane partitioning is not the major factor driving the large difference in the observed permeability curves. Such a small conformational penalty indicates that the entropic cost of selecting a rigid, membrane-soluble conformer among a complex ensemble of aqueous conformers is relatively low even for 10-mers with some degree of flexibility (such as that imparted by two peptoid residues).

Although scaffold (Library) A has low (small) aqueous solubility above A Log P=2, scaffold (Library) B reaches its solubility cliff only above A Log P=4. The large effect of conformation on physiochemical properties, particularly lipophilicity, indicates that two-dimensional (2-D) descriptors such as A Log P may not translate well among different peptide backbones. Instead, each scaffold may need to be interrogated individually to determine the optimal sidechain composition to achieve the desired physiochemical properties.

Without being bound by theory, these results indicate that chameleonicity is not a requirement for high (large) permeability and good (relatively large) aqueous solubility in the bRo5 chemical space. Rigid compounds (such as those of scaffold (Library) A) may be permeable, and at a lower (smaller) overall lipophilicity (A Log P) than is required of more flexible scaffolds (such as the compounds of scaffold (Library) B). For chameleonic macrocycles such as those defined by scaffold (Library) B, permeability is achieved at higher A Log P values, well beyond the solubility limit of their more rigid counterparts.

However, flexibility may be desirable from a biological target binding standpoint, for example, if the backbone (such as of a cyclic polypeptide-polypeptoid ligand) should open to make polar contacts with the target (e.g., to form hydrogen bonds with amino acid residues in a target molecule in an organism). The small conformational penalty associated with the membrane partitioning of scaffold (Library) B also points toward a small entropic penalty that might be incurred upon target binding, even if the target-bound state is among the many "open" conformers observed in the aqueous NMR spectrum.

Model systems such as the two isomeric scaffolds (Libraries A and B) described here provide insight into the physicochemical requirements for achieving drug-like properties in the bRo5 chemical space. Trends in water solubility, CYP (cytochrome) metabolism, plasma protein binding, and passive membrane permeability correlate with a scaffold's chameleonicity. Achievement of favorable properties is possible for rigid and for flexible scaffolds.

In an embodiment, a permeable cyclic decapeptide-peptoid ligand is designed and prepared. The permeable cyclic decapeptide-peptoid ligand is of a class of ligands. It is determined whether a dissociation constant (Kd) of a ligands in the class and a therapeutic target, such as a protein or protein complex, at physiological conditions is minimized (so that binding is maximized) by the ligands being rigid or by the ligands being flexible. This determination can be made based on, for example, computer modeling or crystallographic data of one or more ligands in the class bound to the therapeutic target. If the dissociation constant is minimized by the ligands being rigid, then selections of groups within the class of ligands are made to obtain a rigid permeable cyclic decapeptide-peptoid ligand. If the dissociation constant is minimized by the ligands being flexible, then selections of groups within the class of ligands are made to obtain a flexible permeable cyclic decapeptide-peptoid ligand.

In an embodiment, a permeable cyclic decapeptide-peptoid ligand is designed and prepared. It is determined whether a required minimum aqueous solubility of the ligand requires the ligand to be of an A Log P of at most 1.9 or whether the required minimum aqueous solubility of the ligand allows the ligand to be of an A Log P of greater than 1.9. For example, administration, e.g., oral or intravenous administration, of the ligand to reach a target organ or site within the body of a patient may require a minimum aqueous solubility. For example, achieving a sufficient concentration of the ligand in the intracellular fluid, cytosol, or nucleoplasm may require a minimum aqueous solubility. When the ligand is required to be of an A Log P of at most 1.9, the structure of the ligand can be selected to be that of a compound within Library A. When the ligand is allowed to be of an A Log P of greater than 1.9, the structure of the ligand can be selected to be that of a compound within Library B.

The embodiments illustrated and discussed in this specification are intended only to teach those skilled in the art ways known to the inventors to make and use the invention. Nothing in this specification should be considered as limiting the scope of the invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A compound of a structure

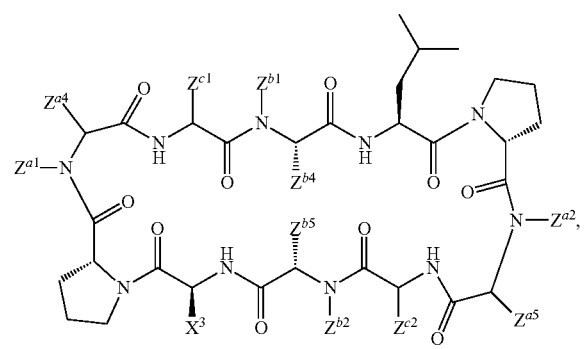

wherein $Z^{a1}$ is $X^1$ or methyl ($CH_3$—),
wherein $Z^{a2}$ is $X^2$ or methyl ($CH_3$—),
wherein $Z^{a4}$ is H or 2-methylpropyl

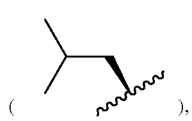

wherein $Z^{a5}$ is H or 2-methylpropyl

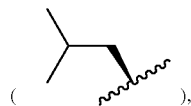

wherein $Z^{b1}$ is $X^1$ or methyl ($CH_3$—),
wherein $Z^{b2}$ is $X^2$ or methyl ($CH_3$—),
wherein $Z^{b4}$ is H or methyl ($CH_3$—),
wherein $Z^{b5}$ is H or methyl ($CH_3$—),
wherein $Z^{c1}$ is 2-methylpropyl

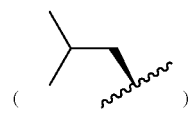

or methyl ($CH_3$—),
wherein $Z^{c2}$ is 2-methylpropyl

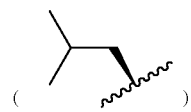

or methyl ($CH_3$—),
wherein $X^1$ is selected from the group consisting of ethyl (Et-)

2-propoxy-3-propyl

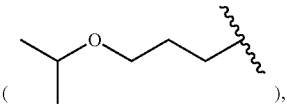 [SMILES: *CCCOC(C)C]

and (1,3-benzodioxol-5-yl)-methyl

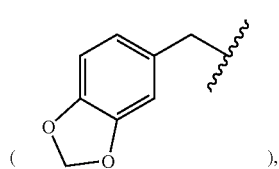

wherein $X^2$ is selected from the group consisting of pentyl

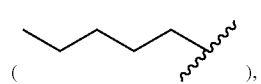

cyclohexylmethyl
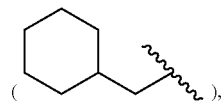 [SMILES: *CC1CCCCC1]
and (oxan-4-yl)methyl
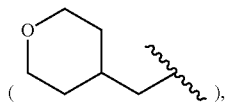
and
wherein $X^3$ is selected from the group consisting of methyl
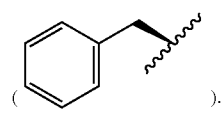
and benzyl
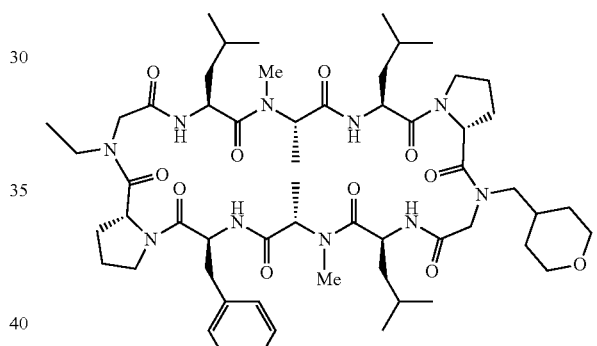
2. The compound of claim 1 of the structure
Library A
3. The compound of claim 1 of the structure
A03
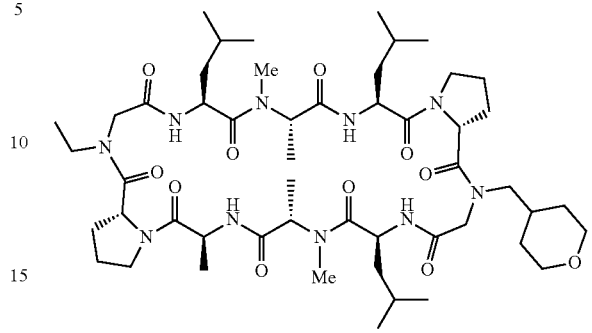
4. The compound of claim 1 of the structure
A09
5. The compound of claim 1 of the structure
A08
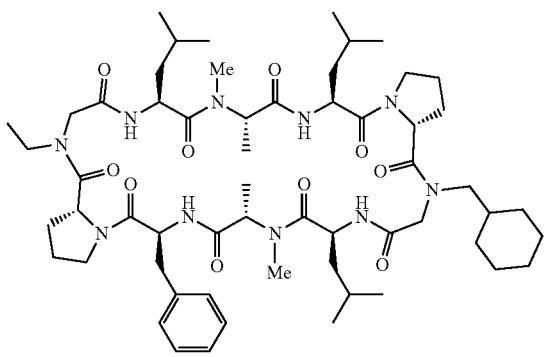

6. The compound of claim 1, of the structure

Library B

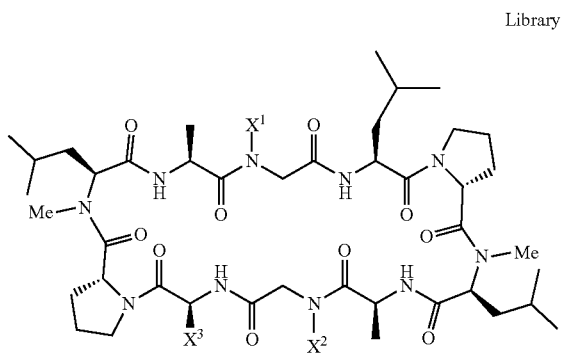

7. The compound of claim 1 of the structure

B09

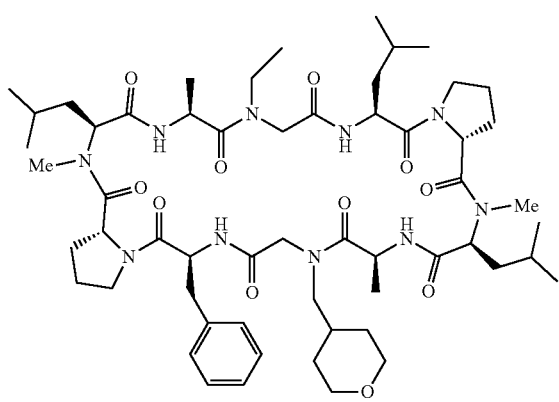

8. The compound of claim 1 of the structure

B08

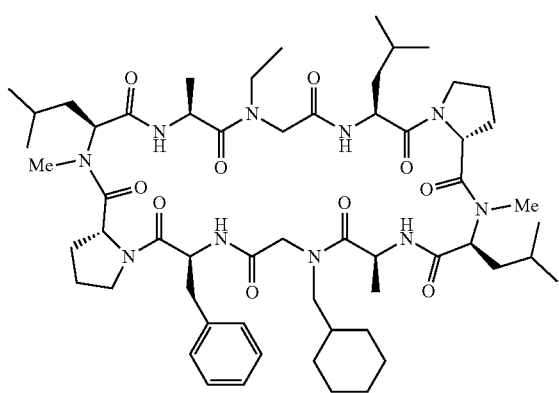

9. The compound of claim 1 of the structure

B03

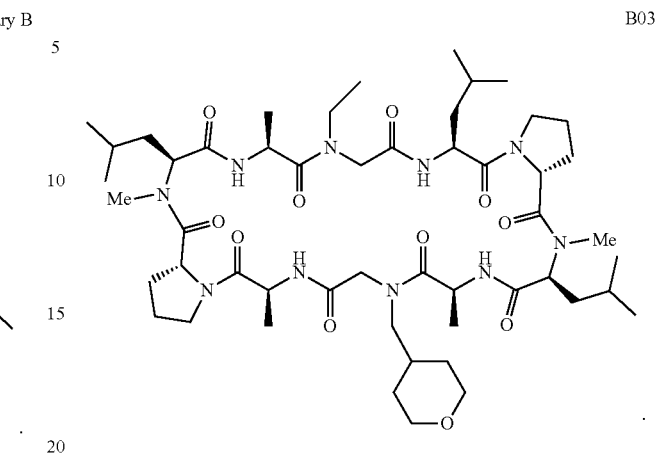

10. The compound of claim 1, wherein $Z^{a1}$ is $X^1$.
11. The compound of claim 10, wherein $X^1$ is ethyl (Et-)

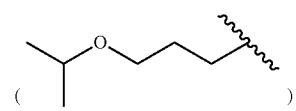 [SMILES: *CCCOC(C)C]

12. The compound of claim 10, wherein $X^1$ is 2-propoxy-3-propyl

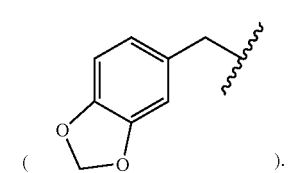 [SMILES: *Cc1ccc2c(c1)OCO2]

or (1,3-benzodioxol-5-yl)-methyl

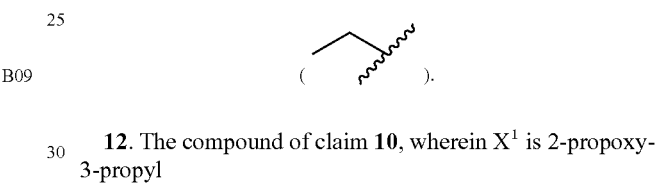

13. The compound of claim 1, wherein $Z^{b1}$ is $X^1$.
14. The compound of claim 13, wherein $X^1$ is ethyl (Et-)

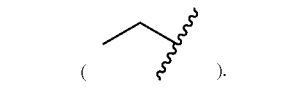

15. The compound of claim 13, wherein $X^1$ is 2-propoxy-3-propyl

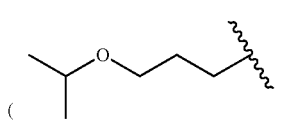

or (1,3-benzodioxol-5-yl)-methyl

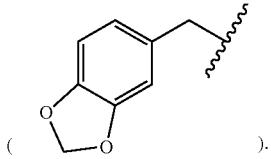 [SMILES: *Cc1ccc2c(c1)OCO2]

16. The compound of claim 1, wherein $Z^{a2}$ is $X^2$.

17. The compound of claim 16, wherein $X^2$ is cyclohexylmethyl

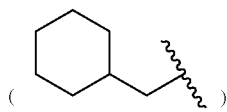 [SMILES: *CC1CCCCC1]

or (oxan-4-yl)methyl

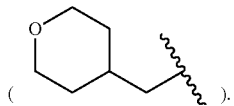

18. The compound of claim 1, wherein $Z^{b2}$ is $X^2$.

19. The compound of claim 18, wherein $X^2$ is cyclohexylmethyl

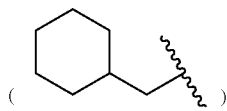 [SMILES: *CC1CCCCC1]

or (oxan-4-yl)methyl

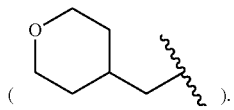

20. The compound of claim 1, wherein $X^3$ is benzyl

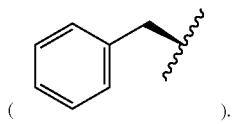

21. A method of designing and preparing a permeable cyclic decapeptide-peptoid ligand, wherein the permeable cyclic decapeptide-peptoid ligand is of a class of ligands of a structure

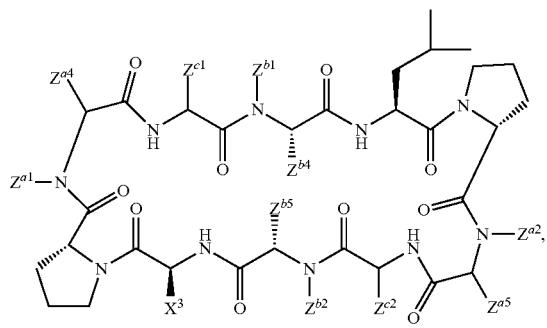

wherein $Z^{a1}$ is $X^1$ or methyl ($CH_3$—),
wherein $Z^{a2}$ is $X^2$ or methyl ($CH_3$—),
wherein $Z^{a4}$ is H or 2-methylpropyl

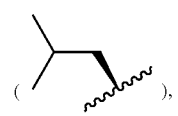

wherein $Z^{a5}$ is H or 2-methylpropyl

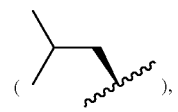

wherein $Z^{b1}$ is $X^1$ or methyl ($CH_3$—),
wherein $Z^{b2}$ is $X^2$ or methyl ($CH_3$—),
wherein $Z^{b4}$ is H or methyl ($CH_3$—),
wherein $Z^{b5}$ is H or methyl ($CH_3$—),
wherein $Z^{c1}$ is 2-methylpropyl

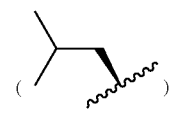

or methyl ($CH_3$—),
wherein $Z^{c2}$ is 2-methylpropyl

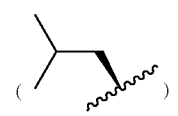

or methyl ($CH_3$—),
wherein $X^1$ is selected from the group consisting of ethyl (Et-)

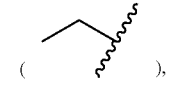 [SMILES: *CC]

2-propoxy-3-propyl

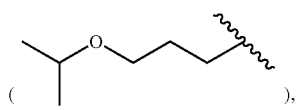 [SMILES: *CCCOC(C)C]

and (1,3-benzodioxol-5-yl)-methyl

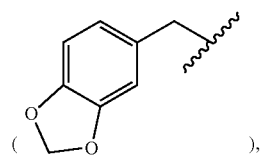

wherein $X^2$ is selected from the group consisting of pentyl

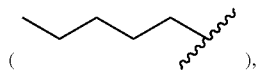

cyclohexylmethyl

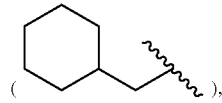

and (oxan-4-yl)methyl

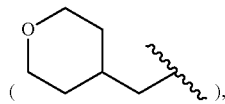 [SMILES: *CC1CCOCC1]

and
wherein $X^3$ is selected from the group consisting of methyl

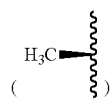

and benzyl

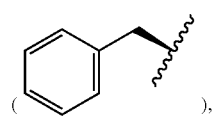

comprising determining whether a dissociation constant of the ligands of the class and a therapeutic target at physiological conditions is minimized by the ligands being rigid or flexible,
when the dissociation constant is minimized by the ligands of the class being rigid, selecting $Z^{a4}$ as H, $Z^{b1}$ as $CH_3$, $Z^{a5}$ as H, and $Z^{b2}$ as $CH_3$ to obtain a rigid permeable cyclic decapeptide-peptoid ligand, when the dissociation constant is minimized by the ligands of the class being flexible, selecting $Z^{a4}$ as 2-methylpropyl, $Z^{b1}$ as $X^1$, $Z^{a5}$ as 2-methylpropyl, and $Z^{b2}$ as $X^2$ to obtain a flexible permeable cyclic decapeptide-peptoid ligand, and synthesizing the permeable cyclic decapeptide-peptoid ligand.

22. The method of claim 21,
wherein when the dissociation constant is minimized by the ligands of the class being rigid, selecting the structure of the permeable cyclic decapeptide-peptoid ligand as

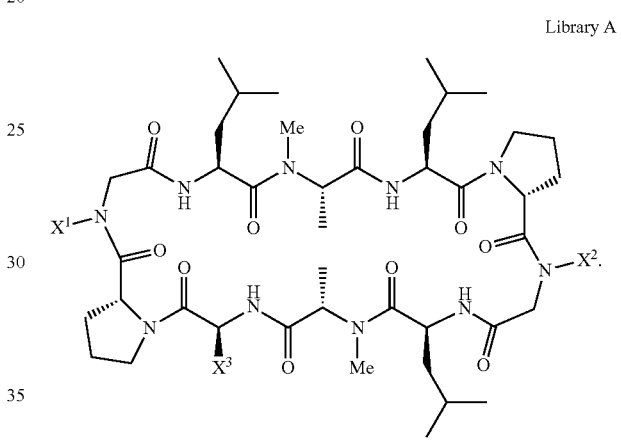

Library A and wherein when the dissociation constant is minimized by the ligands of the class being flexible, selecting the structure of the permeable cyclic decapeptide-peptoid ligand as

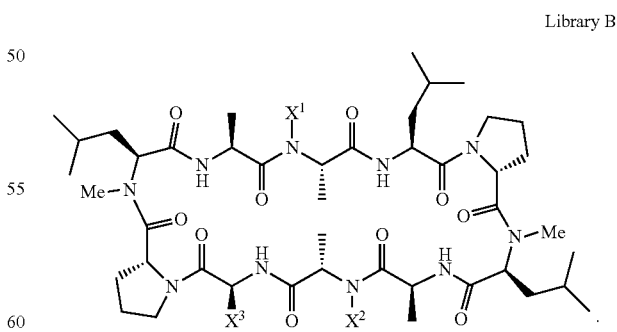

Library B

23. The method of claim 21,
wherein when the dissociation constant is minimized by the ligands of the class being rigid, selecting the structure of the permeable cyclic decapeptide-peptoid ligand as Library A

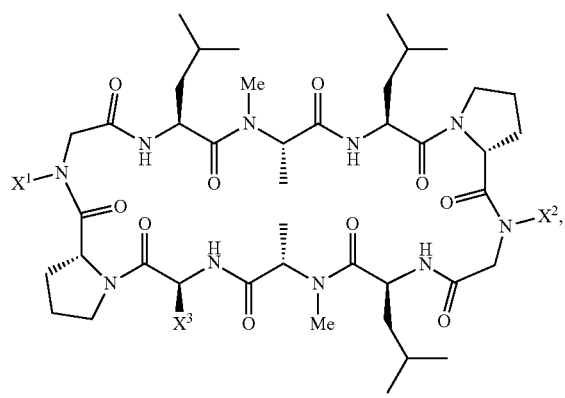

so that the ligand has an A Log P of at most 2.5 and
wherein when the dissociation constant is minimized by the ligand being flexible, selecting the structure of the permeable cyclic decapeptide-peptoid ligand as Library B

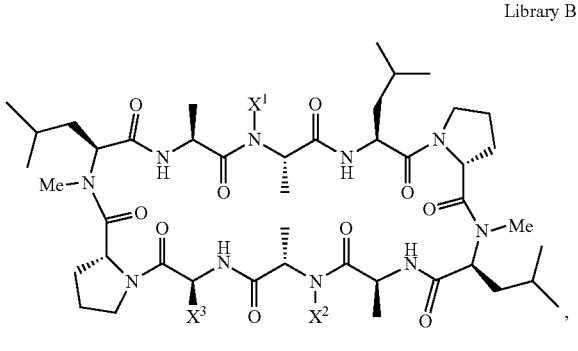

so that the ligand has an A Log P of at least 2.5.

24. The method of claim 21,
wherein when the dissociation constant is minimized by the ligand being rigid, selecting the permeable cyclic decapeptide-peptoid ligand as

A03

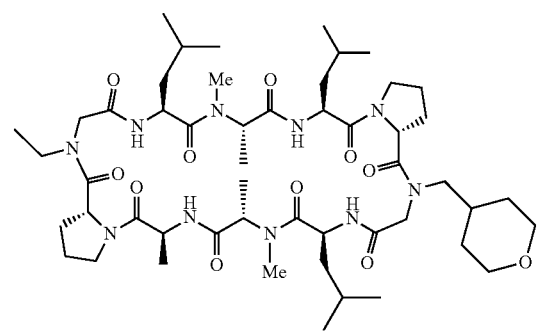

or

A09

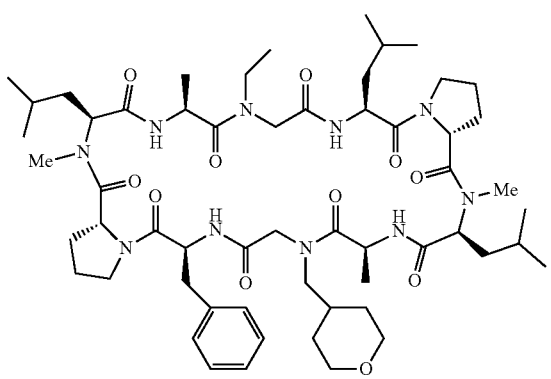

and
wherein when the dissociation constant is minimized by the ligand being flexible, selecting the permeable cyclic decapeptide-peptoid ligand as

B09 or

B08

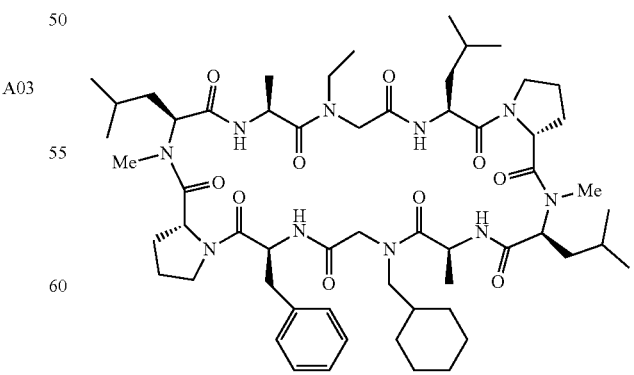

25. A method of designing and preparing a permeable cyclic decapeptide-peptoid ligand of a structure

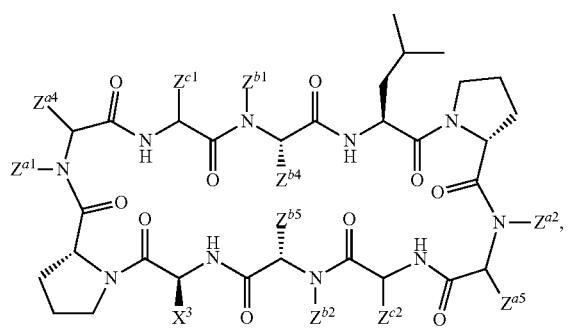

wherein $Z^{a1}$ is $X^1$ or methyl (CH$_3$—),
wherein $Z^{a2}$ is $X^2$ or methyl (CH$_3$—),
wherein $Z^{a4}$ is H or 2-methylpropyl

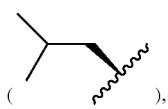

wherein $Z^{a5}$ is H or 2-methylpropyl

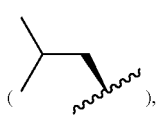

wherein $Z^{b1}$ is $X^1$ or methyl (CH$_3$—),
wherein $Z^{b2}$ is $X^2$ or methyl (CH$_3$—),
wherein $Z^{b4}$ is H or methyl (CH$_3$—),
wherein $Z^{b5}$ is H or methyl (CH$_3$—),
wherein $Z^{c1}$ is 2-methylpropyl

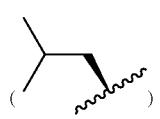

or methyl (CH$_3$—),
wherein $Z^{c2}$ is 2-methylpropyl

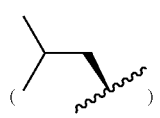

or methyl (CH$_3$—),
wherein $X^1$ is selected from the group consisting of ethyl (Et-)

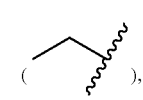

2-propoxy-3-propyl

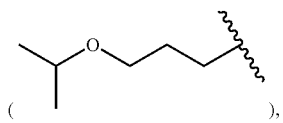

and (1,3-benzodioxol-5-yl)-methyl

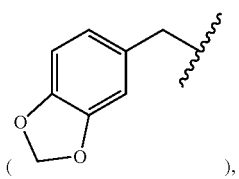

wherein $X^2$ is selected from the group consisting of pentyl

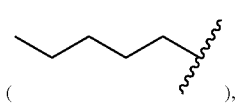

cyclohexylmethyl

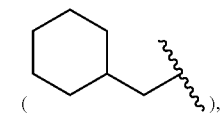

and (oxan-4-yl)methyl

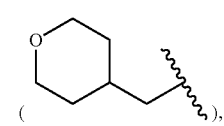 [SMILES: *CC1CCOCC1]

and
wherein $X^3$ is selected from the group consisting of methyl

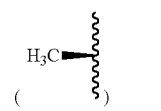

and benzyl

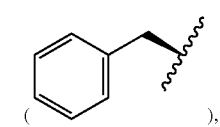

comprising
determining whether a required minimum aqueous solubility of the ligand requires the ligand to be of an A Log P of at most 1.9 or whether the required minimum aqueous solubility of the ligand allows the ligand to be of an A Log P of greater than 1.9, wherein when the ligand is required to be of an A Log P of at most 1.9, selecting $Z^{a4}$ as H, $Z^{b1}$ as $CH_3$, $Z^{a5}$ as H, and $Z^{b2}$ as $CH_3$, wherein when the ligand is allowed to be of an A Log P of greater than 1.9, selecting $Z^{a4}$ as 2-methylpropyl, $Z^{b1}$ as $X^1$, $Z^{a5}$ as 2-methylpropyl, and $Z^{b2}$ as $X^2$, and synthesizing the ligand.

26. The method of claim 25,
wherein when the ligand is required to be of an A Log P of at most 1.9, selecting the structure of the ligand as Library A

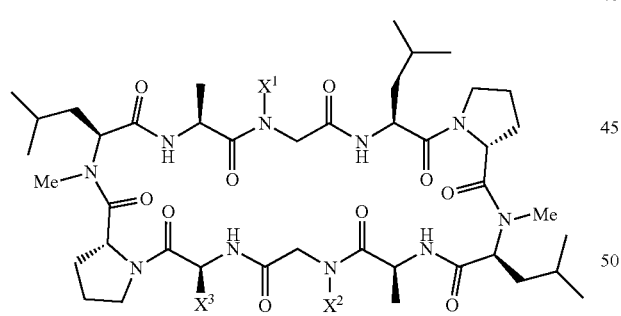

to be of an A Log P of at most 1.9
and
wherein when the ligand is allowed to be of an A Log P of greater than 1.9, selecting the structure of the ligand as Library B

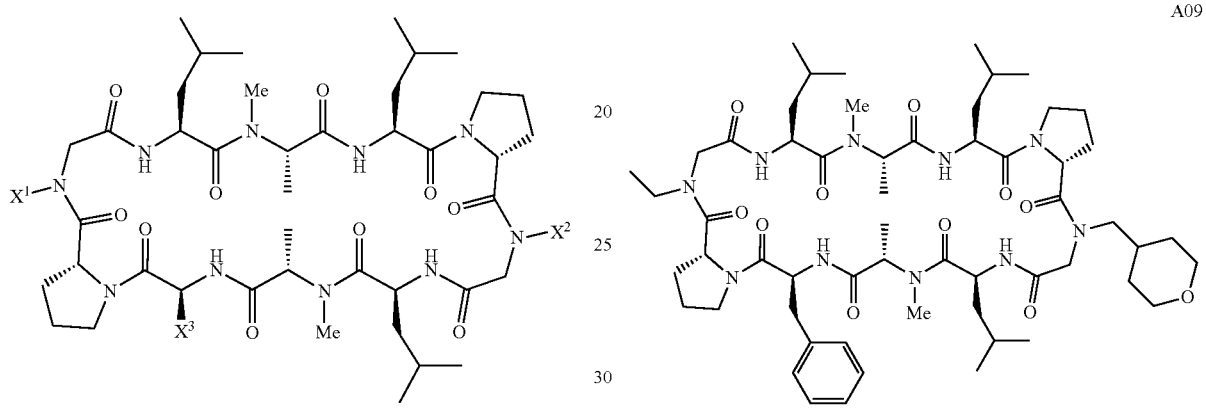

to be of an A Log P of greater than 1.9.

27. The method of claim 25,
wherein when the ligand is required to be of an A Log P of at most 1.9, selecting the ligand as

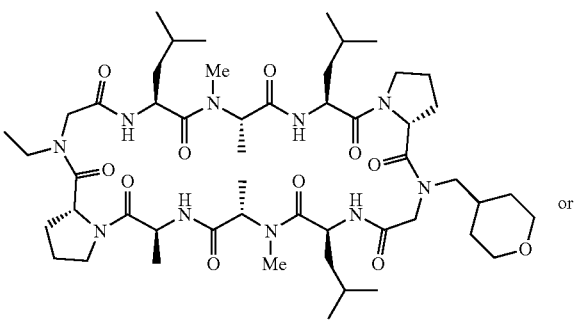

A03 or

A09

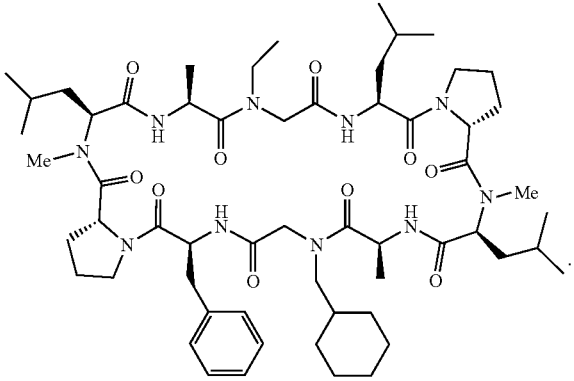

and wherein when the ligand is allowed to be of an A Log P of greater than 1.9, selecting the ligand as

B08

* * * * *

UNITED STATES PATENT AND TRADEMARK OFFICE
CERTIFICATE OF CORRECTION

PATENT NO. : 11,939,403 B2
APPLICATION NO. : 17/366822
DATED : March 26, 2024
INVENTOR(S) : R. Scott Lokey et al.

Page 1 of 2

It is certified that error appears in the above-identified patent and that said Letters Patent is hereby corrected as shown below:

On the Title Page

Left column, Line 8, the inventor's name reading 'R. Lokey' should read -- R. Scott Lokey --.

In the Claims

Claim 22, Column 36, Lines 50 through 60, Library B compound: the chemical structural formula reading ' 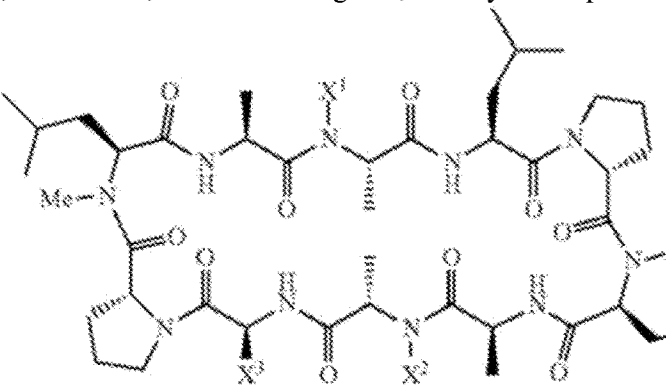 ' should read -- 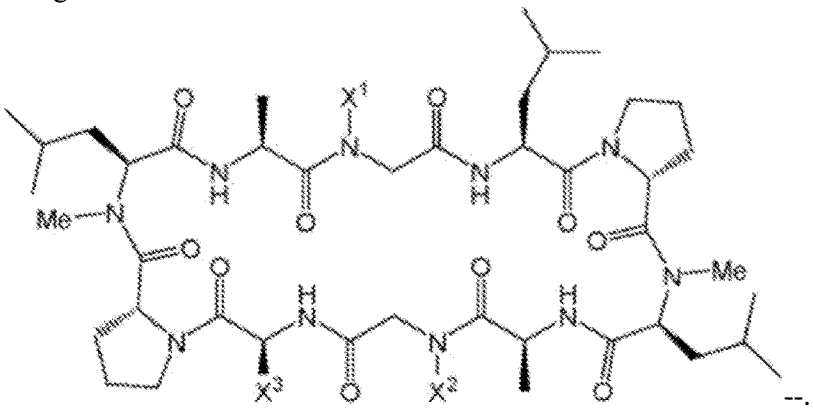 --.

Signed and Sealed this
Seventeenth Day of September, 2024

Katherine Kelly Vidal
*Director of the United States Patent and Trademark Office*

Claim 23, Column 37, Lines 28 through 39, Library B compound: the chemical structural formula reading ' 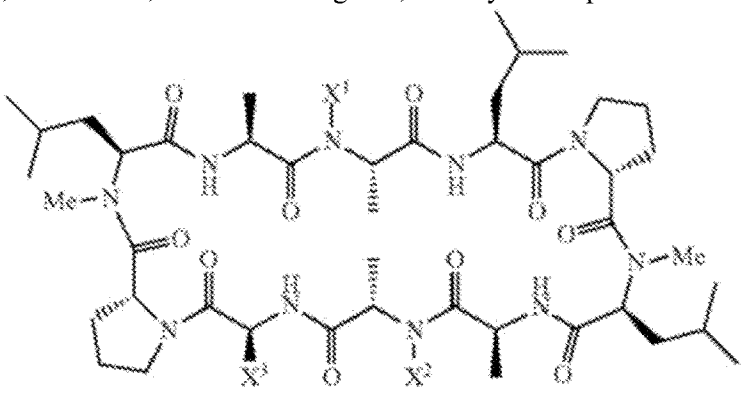 ' should read
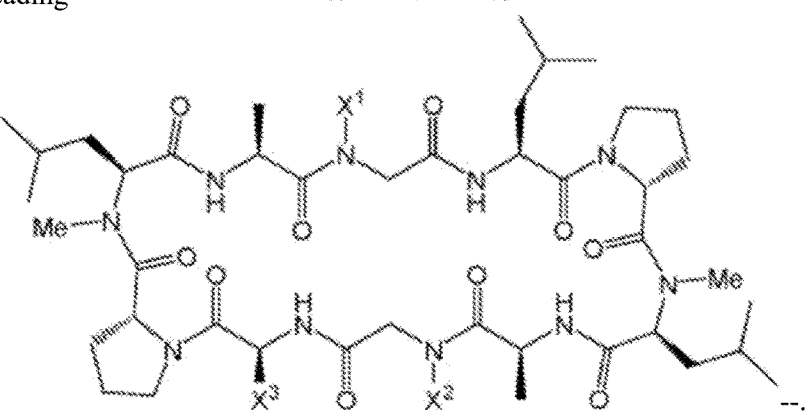
-- --.